(12) United States Patent
Bateman et al.

(10) Patent No.: US 8,569,687 B2
(45) Date of Patent: *Oct. 29, 2013

(54) MASS SPECTROMETER

(71) Applicant: Micromass UK Limited, Manchester (GB)

(72) Inventors: Robert Harold Bateman, Cheshire (GB); Kevin Giles, Cheshire (GB); Steven Derek Pringle, Darwen (GB); Jason Lee Woldgoose, Stockport (GB)

(73) Assignee: Micromass UK Limited, Manchester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/663,191

(22) Filed: Oct. 29, 2012

(65) Prior Publication Data

US 2013/0056629 A1 Mar. 7, 2013

Related U.S. Application Data

(63) Continuation of application No. 12/917,720, filed on Nov. 2, 2010, now Pat. No. 8,299,422, which is a continuation of application No. 11/718,213, filed as application No. PCT/GB2005/004238 on Nov. 3, 2005, now Pat. No. 7,829,841.

(60) Provisional application No. 60/628,215, filed on Nov. 16, 2004.

(30) Foreign Application Priority Data

Nov. 4, 2004 (GB) .................................. 0424426.5

(51) Int. Cl.
*H01J 49/40* (2006.01)
*H01J 49/42* (2006.01)
*H01J 49/00* (2006.01)
*H01J 49/06* (2006.01)

(52) U.S. Cl.
CPC ........... *H01J 49/0027* (2013.01); *H01J 49/004* (2013.01); *H01J 49/065* (2013.01); *H01J 49/40* (2013.01); *H01J 49/42* (2013.01)
USPC ............ 250/281; 250/282; 250/287; 250/292

(58) Field of Classification Search
None
See application file for complete search history.

(56) References Cited

U.S. PATENT DOCUMENTS

| | | | |
|---|---|---|---|
| 5,905,258 A | 5/1999 | Clemmer et al. |
| 6,323,482 B1 | 11/2001 | Clemmer et al. |
| 6,627,883 B2 | 9/2003 | Wang et al. |
| 6,744,043 B2 | 6/2004 | Loboda |
| 6,794,641 B2 | 9/2004 | Bateman et al. |
| 6,891,157 B2 | 5/2005 | Bateman et al. |
| 6,906,319 B2 | 6/2005 | Hoyes |
| 6,992,283 B2 | 1/2006 | Bateman et al. |
| 7,071,467 B2 | 7/2006 | Bateman et al. |
| 7,095,013 B2 | 8/2006 | Bateman et al. |

(Continued)

*Primary Examiner* — Jack Berman
(74) *Attorney, Agent, or Firm* — Diederiks & Whitelaw, PLC

(57) ABSTRACT

A mass spectrometer is disclosed comprising an ion mobility spectrometer or separator and an ion guide arranged downstream of the ion mobility spectrometer or separator. A plurality of axial potential wells are created in the ion guide so that ions received from the ion mobility spectrometer or separator become confined in separate axial potential wells. The potential wells maintain the fidelity and/or composition of ions received from the ion mobility spectrometer or separator. The potential wells are translated along the length of the ion guide.

16 Claims, 17 Drawing Sheets

(56) References Cited

U.S. PATENT DOCUMENTS

| | | |
|---|---|---|
| 7,112,784 B2 | 9/2006 | Bateman et al. |
| 7,205,538 B2 | 4/2007 | Bateman et al. |
| 7,635,841 B2 * | 12/2009 | Bateman et al. .............. 250/292 |
| 7,829,841 B2 | 11/2010 | Bateman et al. |
| 2011/0095175 A1 | 4/2011 | Bateman |

* cited by examiner

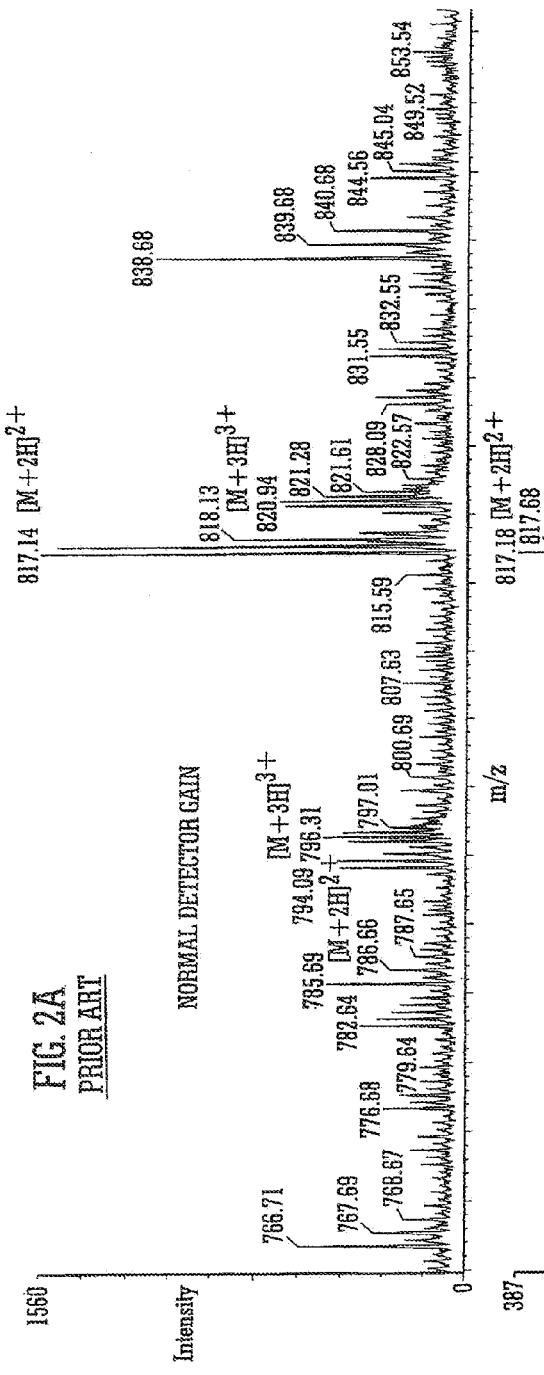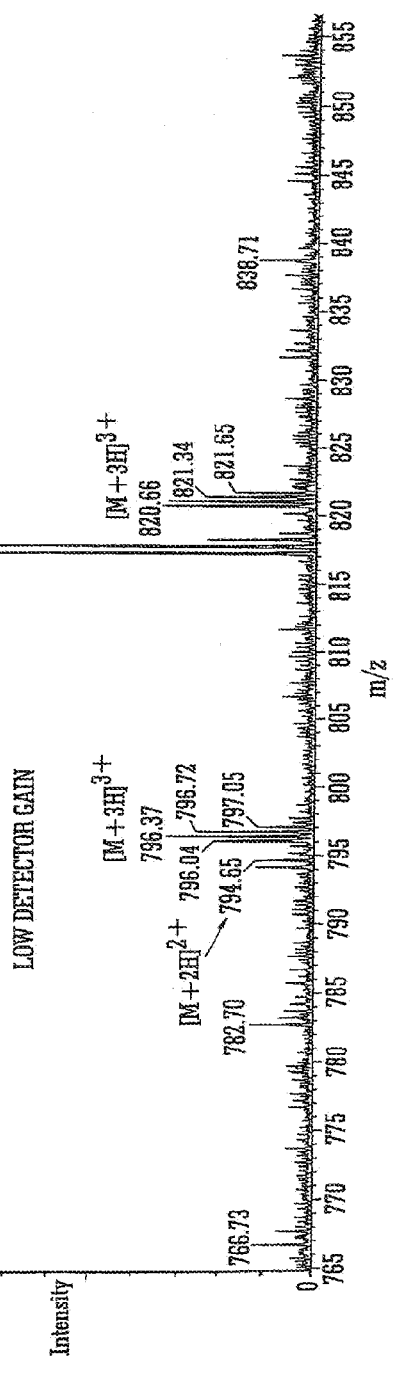
FIG. 2A PRIOR ART
FIG. 2B PRIOR ART

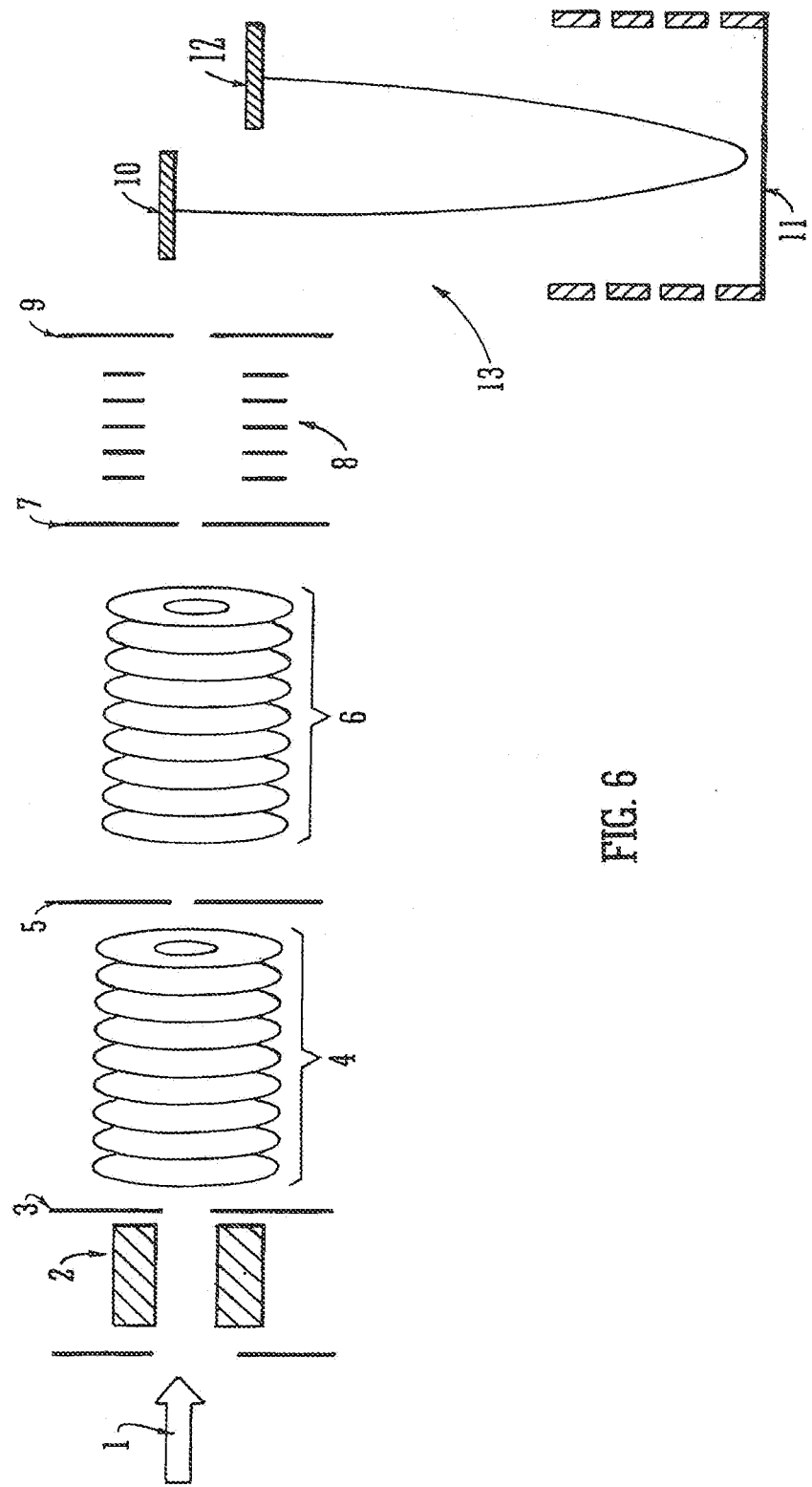

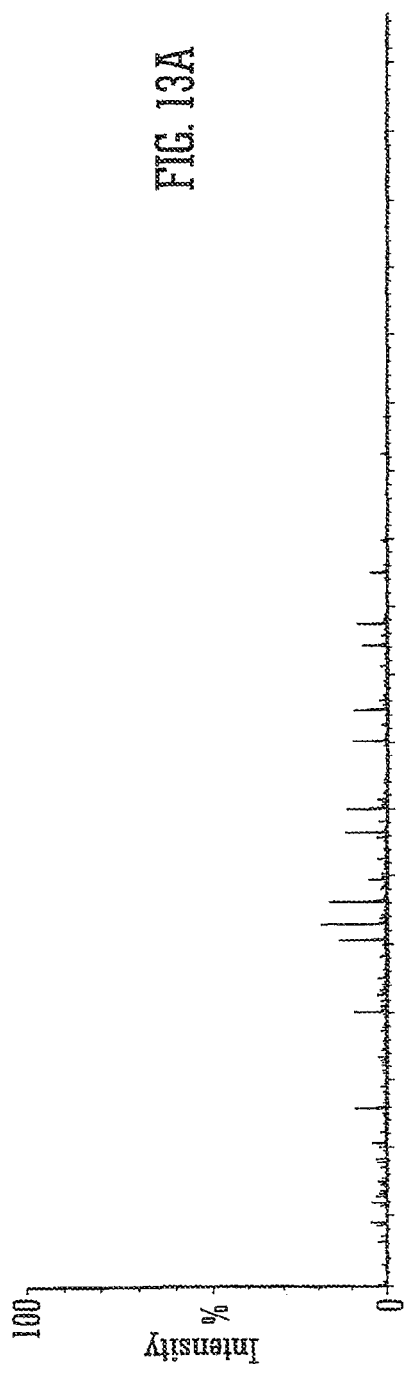
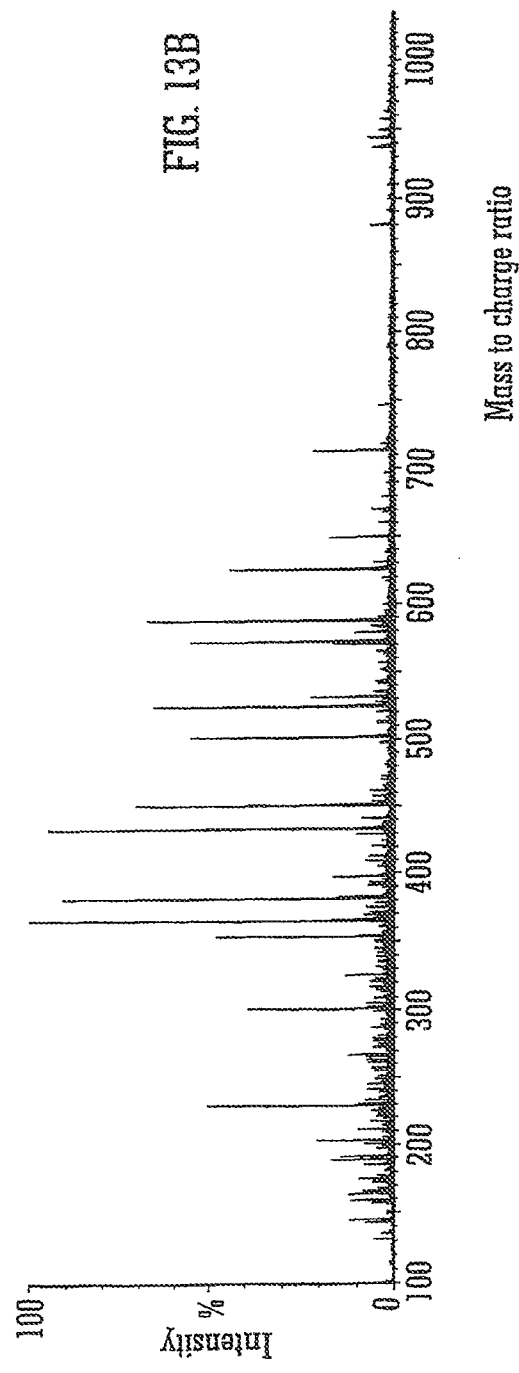

MASS SPECTROMETER

CROSS REFERENCE TO RELATED APPLICATIONS

This application is a continuation of U.S. patent application Ser. No. 12/917,720, filed on Nov. 2, 2010, now U.S. Pat. No. 8,299,427, which is a continuation of U.S. patent application Ser. No. 11/718,213, now U.S. Pat. No. 7,829,841, which is the National Stage of International Application No. PCT/GB2005/004238, filed on Nov. 3, 2005, which claims priority to and benefit of U.S. Provisional Patent Application Ser. No. 60/628,215, filed on Nov. 16, 2004, and priority to and benefit of United Kingdom Patent Application No. 024426, filed Nov. 4, 2004. The entire contents of these applications are incorporated herein by reference.

BACKGROUND OF THE INVENTION

The present invention relates to a mass spectrometer and a method of mass spectrometry.

With the decoding of the 20-30,000 genes that compose the human genome, emphasis has switched to the identification of the translated gene products that comprise the proteome. Mass spectrometry has firmly established itself as the primary technique for identifying proteins due to its unparalleled speed, sensitivity and specificity. Strategies can involve either analysis of the intact protein or more commonly digestion of the protein using a specific protease that cleaves at predictable residues along the peptide backbone. This provides smaller stretches of peptide sequence that are more amenable to analysis via mass spectrometry.

A mass spectrometer comprising an Electrospray Ionisation ("ESI") ion source interfaced to a tandem mass spectrometer has a particularly high degree of specificity and sensitivity. A complex digest mixture may be separated by microcapillary liquid chromatography with on-line mass spectral detection using automated acquisition modes whereby MS and MS/MS spectra may be collected in a data dependant manner. This information may then be used to search databases directly for matching sequences. This may lead to identification of the parent protein especially if the protein is present at low endogenous concentrations. However, often the limiting factor for identification of a protein is not the quality of the MS/MS mass spectrum produced, but rather is the initial recognition of multiply charged peptide parent or precursor ions in the MS mode. This is often due to the relatively high level of largely singly charged background ions emitted by the ion source and which appear in the resulting mass spectrum.

It would therefore be desirable to be able to recognise more easily multiply charged analyte ions of interest which are present in a mixture of ions which may comprise a significant proportion of singly charged background ions.

SUMMARY OF THE INVENTION

According to a first aspect of the present invention there is provided a mass spectrometer comprising:

an ion mobility spectrometer or separator;

a first ion guide arranged downstream of the ion mobility separator or spectrometer, the first ion guide being arranged to receive ions from the ion mobility spectrometer or separator, and wherein the first ion guide comprises a plurality of electrodes;

a first voltage means arranged and adapted to apply one or more voltages or one or more voltage waveforms to the plurality of electrodes so that in a first mode of operation ions received from the ion mobility spectrometer or separator are retained and/or confined and/or transported and/or translated in separate regions or portions of the first ion guide; and a mass analyser arranged downstream of the first guide.

The ion mobility spectrometer or separator preferably comprises a gas phase electrophoresis device. According to a preferred embodiment the ion mobility spectrometer or separator may comprise: (i) a drift tube; (ii) a multipole rod set; (iii) an ion tunnel or on funnel; or (iv) a stack or array of planar, plate or mesh electrodes.

The drift tube preferably comprises one or more electrodes and means for maintaining an axial DC voltage gradient or a substantially constant or linear axial DC voltage gradient along at least 5%, 10%, 15%, 20%, 25%, 30%, 35%, 40%, 45%, 50%, 55%, 60%, 65%, 70%, 75%, 80%, 85%, 90%, 95% or 100% of the axial length of the drift tube.

The multipole rod set preferably comprises a quadrupole rod set, a hexapole rod set, an octapole rod set or a rod set comprising more than eight rods.

The ion tunnel or ion funnel preferably comprises a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area. According to a preferred embodiment at least 5%, 10%, 15%, 20%, 25%, 30%, 35%, 40%, 45%, 50%, 55%, 60%, 65%, 70%, 75%, 80%, 85%, 90%, 95% or 100% of the electrodes have internal diameters or dimensions selected from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; (viii) ≤8.0 mm; (ix) ≤9.0 mm; (x) ≤10.0 mm; and (xi) >10.0 mm.

The stack or array of planar, plate or mesh electrodes preferably comprises a plurality or at least 2, 3, 4, 5, 6, 7, 8, 9, 10, 11, 12, 13, 14, 15, 16, 17, 18, 19, 20 planar, plate or mesh electrodes wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use. According to a preferred embodiment at least some or at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are supplied with an AC or RF voltage and wherein adjacent planar, plate or mesh electrodes are supplied with opposite phases of the AC or RF voltage.

According to a preferred embodiment the ion mobility spectrometer or separator preferably comprises a plurality of axial segments or at least 5, 10, 15, 20, 25, 30, 35, 40, 45, 50, 55, 60, 65, 70, 75, 80, 85, 90, 95 or 100 axial segments.

According to an embodiment the mass spectrometer preferably further comprises DC voltage means for maintaining a substantially constant DC voltage gradient along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator in order to urge at least some ions along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

According to an embodiment the mass spectrometer preferably comprises transient DC voltage means arranged and adapted to apply one or more transient DC voltages or potentials or one or more transient DC voltage or potential waveforms to electrodes forming the ion mobility spectrometer or separator in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

According to an embodiment the mass spectrometer preferably comprises AC or RF voltage means arranged and adapted to apply two or more phase-shifted AC or RF voltages to electrodes forming the ion mobility spectrometer or separator in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

The ion mobility spectrometer or separator preferably has an axial length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; (xvi) >300 mm.

According to a preferred embodiment the ion mobility spectrometer or separator preferably further comprises AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the plurality of electrodes of the ion mobility spectrometer or separator in order to confine ions radially within the ion mobility spectrometer or separator. The AC or RF voltage means is preferably arranged and adapted to supply an AC or RF voltage to the plurality of electrodes of the ion mobility spectrometer or separator having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak. The AC or RF voltage means is preferably arranged and adapted to supply an AC or RF voltage to the plurality of electrodes of the ion mobility spectrometer or separator having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

According to a preferred embodiment singly charged ions having a mass to charge ratio in the range of 0-100, 100-200, 200-300, 300-400, 400-500, 500-600, 600-700, 700-800, 800-900 or 900-1000 preferably have a drift or transit time through the ion mobility spectrometer or separator in the range: (i) 0-1 ms; (ii) 1-2 ms; (iii) 2-3 ms; (iv) 3-4 ms; (v) 4-5 ms; (vi) 5-6 ms; (vii) 6-7 ms; (viii) 7-8 ms; (ix) 8-9 ms; (x) 9-10 ms; (xi) 10-11 ms; (xii) 11-12 ms; (xiii) 12-13 ms; (xiv) 13-14 ms; (xv) 14-15 ms; (xvi) 15-16 ms; (xvii) 16-17 ms; (xviii) 17-18 ms; (xix) 18-19 ms; (xx) 19-20 ms; (xxi) 20-21 ms; (xxii) 21-22 ms; (xxiii) 22-23 ms; (xxiv) 23-24 ms; (xxv) 24-25 ms; (xxvi) 25-26 ms; (xxvii) 26-27 ms; (xxviii) 27-28 ms; (xxix) 28-29 ms; (xxx) 29-30 ms; and (xxxi) >30 ms.

The mass spectrometer preferably further comprises means arranged and adapted to maintain at least a portion of the ion mobility spectrometer or separator at a pressure selected from the group consisting of: (i) >0.001 mbar; (ii) >0.01 mbar; (iii) >0.1 mbar; (iv) >1 mbar; (v) >10 mbar; (vi) >100 mbar; (vii) 0.001-100 mbar; (viii) 0.01-10 mbar; and (ix) 0.1-1 mbar.

The mass spectrometer preferably further comprises means for introducing a first gas into the ion mobility spectrometer or separator, the first gas being selected from or at least partially comprising a gas selected from the group consisting of: (i) nitrogen; (ii) argon; (iii) helium; (iv) methane; (v) neon; (vi) xenon; and (vii) air.

According to a preferred embodiment the mass spectrometer preferably further comprises a housing for the ion mobility spectrometer or separator. The housing preferably forms a substantially gas tight enclosure apart from an ion entrance aperture, an ion exit aperture and a port for introducing a gas into the housing.

The mass spectrometer preferably further comprises means for pulsing ions into the ion mobility spectrometer or separator once every 0-5 ms, 5-10 ms, 10-15 ms, 15-20 ms, 20-25 ms, 25-30 ms, 30-35 ms, 35-40 ms, 40-45 ms, 45-50 ms or >50 ms.

The first ion guide preferably comprises: (i) a multipole rod set or a segmented multipole rod set; (ii) an ion tunnel or ion funnel; or (iii) a stack or array of planar, plate or mesh electrodes.

According to an embodiment of the present invention a second ion guide may be arranged upstream of the ion mobility spectrometer or separator. The second ion guide preferably comprises: (i) a multipole rod set or a segmented multipole rod set; (ii) an ion tunnel or ion funnel; or (iii) a stack or array of planar, plate or mesh electrodes.

The first and/or second ion guide may comprise a multipole rod set comprising a quadrupole rod set, a hexapole rod set, an octapole rod set or a rod set comprising more than eight rods.

The first and/or second ion guide may comprise an ion tunnel or ion tunnel comprises a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area. Preferably, at least 5%, 10%, 15%, 20%, 25%, 30%, 35%, 40%, 45%, 50%, 55%, 60%, 65%, 70%, 75%, 80%, 85%, 90%, 95% or 100% of the electrodes have internal diameters or dimensions selected from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; (viii) ≤8.0 mm; (ix) ≤9.0 mm; (x) ≤10.0 mm; and (xi) >10.0 mm.

The first and/or second ion guides may comprise a stack or array of planar, plate or mesh electrodes preferably comprising a plurality or at least 2, 3, 4, 5, 6, 7, 8, 9, 10, 11, 12, 13, 14, 15, 16, 17, 18, 19 or 20 planar, plate or mesh electrodes arranged generally in the plane in which ions travel in use, wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use. According to a preferred embodiment the mass spectrometer preferably further comprises AC or RF voltage means for supplying the plurality of planar, plate or mesh electrodes with an AC or RF voltage and wherein adjacent plate or mesh electrodes are supplied with opposite phases of the AC or RF voltage.

According to the preferred embodiment the first and/or second ion guide may comprise a plurality of axial segments or at least 5, 10, 15, 20, 25, 30, 35, 40, 45, 50, 55, 60, 65, 70, 75, 80, 85, 90, 95 or 100 axial segments.

According to the preferred embodiment the mass spectrometer may further comprise transient DC voltage means arranged and adapted to apply one or more transient DC voltages or potentials or one or more transient DC voltage or potential waveforms to electrodes forming the first and/or second ion guides in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the first and/or second ion guide.

According to the preferred embodiment the mass spectrometer may preferably further comprise AC or RF voltage means arranged and adapted to apply two or more phase-shifted AC or RF voltages to electrodes forming the first and/or second ion guide in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the first and/or second ion guide.

The first and/or second ion guide preferably has an axial length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm.

The first and/or second ion guide preferably further comprises AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the plurality of electrodes of the first and/or second ion guide in order to confine ions radially within the first and/or second ion guide. The AC or RF voltage means is preferably arranged and adapted to supply an AC or RF voltage to the plurality of electrodes of the first and/or second ion guide having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak. The AC or RF voltage means is preferably arranged and adapted to supply an AC or RF voltage to the plurality of electrodes of the first and/or second ion guide having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

According to the preferred embodiment singly charged ions having a mass to charge ratio in the range of 1-100, 100-200, 200-300, 300-400, 400-500, 500-600, 600-700, 700-800, 800-900 or 900-1000 preferably have a drift or transit time through the first and/or second ion guide in the range: (i) 0-10 μs; (ii) 10-20 μs; (iii) 20-30 μs; (iv) 30-40 μs; (v) 40-50 μs; (vi) 50-60 μs; (vii) 60-70 μs; (viii) 70-80 μs; (ix) 80-90 μs; (x) 90-100 μs; (xi) 100-110 μs; (xii) 110-120 μs; (xiii) 120-130 μs; (xiv) 130-140 μs; (xv) 140-150 μs; (xvi) 150-160 μs; (xvii) 160-170 μs; (xviii) 170-180 μs; (xix) 180-190 μs; (xx) 190-200 μs; (xxi) 200-210 μs; (xxii) 210-220 μs; (xxiii) 220-230 μs; (xxiv) 230-240 μs; (xxv) 240-250 μs; (xxvi) 250-260 μs; (xxvii) 260-270 μs; (xxviii) 270-280 μs; (xxix) 280-290 μs; (xxx) 290-300 μs; and (xxxi) >300 μs.

According to the preferred embodiment the mass spectrometer preferably further comprises means arranged and adapted to maintain at least a portion of the first and/or second ion guide at a pressure selected from the group consisting of: (i) >0.0001 mbar; (ii) >0.001 mbar; (iii) >0.01 mbar; (iv) >0.1 mbar; (v) >1 mbar; (vi) >10 mbar; (vii) 0.0001-0.1 mbar; and (viii) 0.001-0.01 mbar.

The mass spectrometer preferably further comprises acceleration means arranged and adapted to accelerate ions emerging from the ion mobility spectrometer or separator into the first ion guide and wherein in a second mode of operation at least 5%, 10%, 15%, 20%, 25%, 30%, 35%, 40%, 45%, 50%, 55%, 60%, 65%, 70%, 75%, 80%, 85%, 90%, 95% or 100% of the ions are caused to fragment upon entering the first ion guide. The acceleration means is preferably arranged and adapted to progressively vary or increase the kinetic energy of ions emerging from the ion mobility spectrometer or separator as they are transmitted to the first ion guide. The acceleration means preferably comprises a region across which a potential difference is maintained and wherein the potential difference is progressively varied or increased with time.

The mass spectrometer preferably further comprises a control system arranged and adapted to switch or repeatedly switch the potential difference through which ions pass prior to entering the first ion guide between a high fragmentation mode of operation wherein ions are substantially fragmented upon entering the first ion guide and a low fragmentation mode of operation wherein substantially less ions are fragmented or wherein substantially no ions are fragmented upon entering the first ion guide.

In the high fragmentation mode of operation ions entering the first ion guide are preferably accelerated through a potential difference selected from the group consisting of: (i) ≥10 V; (ii) ≥20 V; (iii) ≥30 V; (iv) ≥40 V; (v) ≥50 V; (vi) ≥60 V; (vii) ≥70 V; (viii) ≥80 V; (ix) ≥90 V; (x) ≥100 V; (xi) ≥110 V; (xii) ≥120 V; (xiii) ≥130 V; (xiv) ≥140 V; (xv) ≥150 V; (xvi) ≥160 V; (xvii) ≥170 V; (xviii) ≥180 V; (xix) ≥190 V; and (xx) ≥200 V.

In the low fragmentation mode of operation ions entering the first ion guide are preferably accelerated through a potential difference selected from the group consisting of: (i) ≤20 V; (ii) ≤15 V; (iii) ≤10 V; (iv) ≤5V; and (v) ≤1V.

The control system is preferably arranged and adapted to switch the first ion guide between a high fragmentation mode of operation and a low fragmentation mode of operation at least once every 1 ms, 5 ms, 10 ms, 15 ms, 20 ms, 25 ms, 30 ms, 35 ms, 40 ms, 45 ms, 50 ms, 55 ms, 60 ms, 65 ms, 70 ms, 75 ms, 80 ms, 85 ms, 90 ms, 95 ms, 100 ms, 200 ms, 300 ms, 400 ms, 500 ms, 600 ms, 700 ms, 800 ms, 900 ms, 1 s, 2 s, 3 s, 4 s, 5 s, 6 s, 7 s, 8 s, 9 s or 10 s.

The first ion guide is preferably arranged and adapted to receive a beam of ions from the ion mobility spectrometer or separator and to convert or partition the beam of ions such that at least 1, 2, 3, 4, 5, 6, 7, 8, 9, 10, 11, 12, 13, 14, 15, 16, 17, 18, 19 or 20 separate groups or packets of ions are confined and/or isolated in the first ion guide at any particular time, and wherein each group or packet of ions is separately confined and/or isolated in a separate axial potential well formed in the first ion guide. The average ion mobility of ions in each of the groups or packets of ions confined and/or isolated in the first ion guide preferably progressively decreases with time and/or progressively decreases from the exit region of the first ion guide towards the entrance region of the first ion guide.

The first voltage means is preferably arranged and adapted to create at least 1, 2, 3, 4, 5, 6, 7, 8, 9, 10, 11, 12, 13, 14, 15, 16, 17, 18, 19 or 20 separate axial potential wells which are preferably substantially simultaneously translated along at least 5%, 10%, 15%, 20%, 25%, 30%, 35%, 40%, 45%, 50%, 55%, 60%, 65%, 70%, 75%, 80%, 85%, 90%, 95% or 100% of the length of the first ion guide.

A second voltage means is preferably arranged and adapted to create at least 1, 2, 3, 4, 5, 6, 7, 8, 9, 10, 11, 12, 13, 14, 15, 16, 17, 18, 19 or 20 separate axial potential wells which are preferably substantially simultaneously translated along at least 5%, 10%, 15%, 20%, 25%, 30%, 35%, 40%, 45%, 50%, 55%, 60%, 65%, 70%, 75%, 80%, 85%, 90%, 95% or 100% of the length of the second ion guide.

The first ion guide is preferably arranged and adapted to retain and/or confine and/or partition ions emerging from the ion mobility spectrometer or separator and to translate ions in one or more groups or packets of ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the first ion guide whilst either: (i) substantially maintaining the order and/or fidelity in which ions emerge from the ion mobility spectrometer or separator; and/or (ii) substantially maintaining the composition of ions as one or more groups or packets of ions are translated along the first ion guide.

According to the preferred embodiment the mass spectrometer preferably further comprises an ion trap upstream of the ion mobility spectrometer or separator. The ion trap is preferably arranged and adapted to repeatedly pulse ions into the ion mobility spectrometer or separator.

According to the preferred embodiment the second ion guide preferably has a cycle time which either: (i) substantially corresponds with a cycle time of the ion mobility spectrometer or separator; or (ii) substantially differs from a cycle time of the ion mobility spectrometer or separator.

In a mode of operation the second on guide is preferably arranged and adapted to trap, store or accumulate ions in an ion trapping region located towards, near or substantially at the exit of the second ion guide. Ions are preferably periodically released from the ion trapping region of the second ion guide and are preferably passed to the ion mobility spectrometer or separator.

The mass spectrometer preferably comprises means arranged and adapted to maintain at least a portion of the second ion guide at a pressure selected from the group consisting of: (i) >0.0001 mbar; (ii) >0.001 mbar; (iii) >0.01 mbar; (iv) >0.1 mbar; (v) >1 mbar; (vi) >10 mbar; (vii) 0.0001-0.1 mbar; and (viii) 0.001-0.01 mbar.

The mass spectrometer preferably comprises acceleration means arranged and adapted to accelerate ions into the second ion guide so that at least some ions are caused to fragment upon entering the second ion guide. The mass spectrometer preferably further comprises means arranged and adapted to optimise the energy of ions prior to entering the second ion guide so that the ions are preferably caused to fragment in a substantially optimal manner.

According to the preferred embodiment there is provided a control system arranged and adapted to switch or repeatedly switch the potential difference through which ions pass prior to entering the second ion guide between a first mode of operation wherein ions are substantially fragmented upon entering the second ion guide and a second mode of operation wherein substantially less ions are fragmented or wherein substantially no ions are fragmented upon entering the second ion guide.

In the first mode of operation ions entering the second ion guide are preferably accelerated through a potential difference selected from the group consisting of: (i) ≥10 V; (ii) ≥20 V; (iii) ≥30 V; (iv) ≥40 V; (v) ≥50 V; (vi) ≥60 V; (vii) ≥70 V; (viii) ≥80 V; (ix) ≥90 V; (x) ≥100 V; (xi) ≥110 V; (xii) ≥120 V; (xiii) ≥130 V; (xiv) ≥140 V; (xv) ≥150 V; (xvi) ≥160 V; (xvii) ≥170 V; (xviii) ≥180 V; (xix)≥190 V; and (xx) ≥200 V.

In the second mode of operation ions entering the second ion guide are preferably accelerated through a potential difference selected from the group consisting of: (i) ≤20 V; (ii) ≤15 V; (iii) ≤10 V; (iv) ≤5V; and (v) ≤1V.

The control system is preferably arranged and adapted to switch the second ion guide between the first mode of operation and the second mode of operation at least once every 1 ms, 5 ms, 10 ms, 15 ms, 20 ms, 25 ms, 30 ms, 35 ms, 40 ms, 45 ms, 50 ms, 55 ms, 60 ms, 65 ms, 70 ms, 75 ms, 80 ms, 85 ms, 90 ms, 95 ms, 100 ms, 200 ms, 300 ms, 400 ms, 500 ms, 600 ms, 700 ms, 800 ms, 900 ms, 1 s, 2 s, 3 s, 4 s, 5 s, 6 s, 7 s, 8 s, 9 s or 10 s.

According to an embodiment the mass spectrometer preferably further comprises a fragmentation or collision cell for fragmenting ions by Collision Induced Dissociation ("CID") upon colliding with or impacting gas or other molecules.

According to an alternative embodiment the mass spectrometer preferably further comprises a fragmentation device for fragmenting ions, the fragmentation device selected from the group consisting of: (i) a Surface Induced Dissociation ("SID") fragmentation device; (ii) an Electron Transfer Dissociation fragmentation device; (iii) an Electron Capture Dissociation 11 fragmentation device; (iv) an Electron Collision or Impact Dissociation fragmentation device; (v) a Photo Induced Dissociation ("PID") fragmentation device; (vi) a Laser induced Dissociation fragmentation device; (vii) an infrared radiation induced dissociation device; (viii) an ultraviolet radiation induced dissociation device; (ix) an ion-molecule reaction fragmentation device; (x) a nozzle-skimmer interface fragmentation device; (xi) an in-source fragmentation device; (xii) an ion-source Collision Induced Dissociation fragmentation device; (xiii) a thermal or temperature source fragmentation device; (xiv) an electric field induced fragmentation device; (xv) a magnetic field induced fragmentation device; and (xvi) an enzyme digestion or enzyme degradation fragmentation device.

According to a preferred embodiment the mass spectrometer preferably further comprises a mass filter, a quadrupole rod set mass filter, a Time of Flight mass analyser, a Wein filter or a magnetic sector mass analyser arranged upstream and/or downstream of the second ion guide.

A further ion guide may be provided upstream and/or downstream of the second ion guide and is preferably arranged upstream of a mass filter and downstream of an ion source.

The further ion guide preferably comprises: (i) a multipole rod set or a segmented multipole rod set; (ii) an ion tunnel or ion funnel; or (iii) a stack or array of planar, plate or mesh electrodes.

The multipole rod set preferably comprises a quadrupole rod set, a hexapole rod set, an octopole rod set or a rod set comprising more than eight rods.

The ion tunnel or ion tunnel preferably comprises a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/ or smaller in size or in area. Preferably, at least 5%, 10%, 15%, 20%, 25%, 30%, 35%, 40%, 45%, 50%, 55%, 60%, 65%, 70%, 75%, 80%, 85%, 90%, 95% or 100% of the electrodes have internal diameters or dimensions selected from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; (viii) ≤8.0 mm; (ix) ≤9.0 mm; (x) ≤10.0 mm; and (xi) a >10.0 mm.

The stack or array of planar, plate or mesh electrodes preferably comprises a plurality or at least 2, 3, 4, 5, 6, 7, 8, 9, 10, 11, 12, 13, 14, 15, 16, 17, 18, 19 or 20 planar, plate or mesh electrodes arranged generally in the plane in which ions travel in use, wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use. The mass spectrometer preferably further comprises AC or RF voltage means for supplying the plurality of planar, plate or mesh electrodes with an AC or RF voltage and wherein adjacent plate or mesh electrodes are supplied with opposite phases of the AC or RF voltage.

The further ion guide preferably further comprises a plurality of axial segments or at least 5, 10, 15, 20, 25, 30, 35, 40, 45, 50, 55, 60, 65, 70, 75, 80, 85, 90, 95 or 100 axial segments.

Transient DC voltage means may be arranged and adapted to apply one or more transient DC voltages or potentials or one or more transient DC voltage or potential waveforms to electrodes forming the further ion guide in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the further ion guide. Alternatively, AC or RF voltage means may be provided which are preferably arranged and adapted to apply two or more phase-shifted AC or RF voltages to electrodes forming the further ion guide in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the further ion guide.

The mass spectrometer preferably further comprises a transfer device, an Einzel lens or ion optical lens arrangement arranged between the first ion guide and the mass analyser.

The mass spectrometer preferably further comprises an ion source. The ion source may be selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption ionisation On Silicon ("DIOS") ion source; (viii) an Electron Impact ("EI") ion source; (ix) a Chemical Ionisation. ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary ion Mass Spectrometry ("LSIMS") ion source; (xv) a Desorption Electrospray Ionisation ("DESI") ion source; (xvi) a Nickel-63 radioactive ion source; and (xvii) an Atmospheric Pressure Matrix Assisted Laser Desorption Ionisation ion source. The ion source may comprise a pulsed or continuous ion source.

The mass analyser preferably comprises a Time of Flight mass analyser or an axial or orthogonal acceleration Time of Flight mass analyser. The mass analyser preferably comprises a pusher and/or puller electrode wherein ions are released from the first ion guide into the Time of Flight mass analyser at a first time and arrive in a region in the vicinity of the pusher and/or puller electrode. The pusher and/or puller electrode is then preferably energized after a delay time subsequent to the first time. The mass analyser is preferably arranged and adapted such that the delay time is preferably progressively varied or increased. The delay time may be set such "that ions having a desired charge state are substantially orthogonally accelerated whereas ions having an undesired charge state are not substantially orthogonally accelerated. The desired charge state and/or the undesired charge state may be selected from the group consisting of: (i) ions having a single charge; (ii) ions having two charges; (iii) ions having three charges; (iv) ions having four charges; (v) ions having five charges; (vi) ions having more than five charges; and (vii) multiply charged ions.

A first plurality of ions are preferably pulsed into the ion mobility spectrometer or separator and prior to a second plurality of ions being pulsed into the ion mobility spectrometer or separator the pusher and/or puller electrode is preferably energised at least x times, wherein x is selected from the group consisting of: (i) 1; (ii) 2-10; (iii) 10-20; (iv) 20-30; (v) 30-40; (vi) 40-50; (viii) 50-60; (ix) 60-70; (x) 70-80; (xi) 80-90; (xii) 90-100; (xiii) 100-110; (xiv) 110-120; (xv) 120-130; (xvi) 130-140; (xvii) 140-150; (xviii) 150-160; (xix) 160-170; (xx) 170-180; (xxi) 180-190; (xxii) 190-200; (xxiii) 200-210; (xxiv) 210-220; (xxv) 220-230; (xxvi) 230-240; (xxvii) 240-250; and (xxviii) >250.

The pusher and/or puller electrode is preferably energized once every 0-10 μs, 10-20 μs, 20-30 μs, 30-40 μs, 40-50 μs, 50-60 μs, 60-70 μs, 70-80 μs, 80-90 μs, 90-100 μs, 100-110 μs, 110-120 μs, 120-130 μs, 130-140 μs, 140-150 μs, 150-160 μs, 160-170 μs, 170-180 μs, 180-190 μs, 190-200 μs, 200-210 μs, 210-220 μs, 220-230 μs, 230-240 μs, 240-250 μs, 250-260 μs, 260-270 μs, 270-280 μs, 280-290 μs 290-300 μs or >300 μs.

The pusher and/or puller electrode is preferably energized at least 1, 2, 3, 4, 5, 6, 7, 8, 9, 10, 11, 12, 13, 14, 15, 16, 17, 18, 19, 20 or >20 times for every 1, 2, 3, 4, 5, 6, 7, 8, 9, 10, 11, 12, 13, 14, 15, 16, 17, 18, 19, 20 or >20 axial potential wells which are translated to the end of the first ion guide such that ions are caused to be emitted or otherwise ejected from the first ion guide.

According to the preferred embodiment a first plurality of ions are pulsed into the ion mobility spectrometer or separator and prior to a second plurality of ions being pulsed into the ion mobility spectrometer or separator at least y separate axial potential wells are created or formed in the first ion guide and/or are translated along at least a portion of the axial length of the first ion guide, wherein y is selected from the group consisting of: (i) 1; (ii) 2-10; (iii) 10-20; (iv) 20-30; (v) 30-40; (vi) 40-50; (viii) 50-60; (ix) 60-70; (x) 70-80; (xi) 80-90; (xii) 90-100; (xiii) 100-110; (xiv) 110-120; (xv) 120-130; (xvi) 130-140; (xvii) 140-150; (xviii) 150-160; (xix) 160-170; (XX) 170-180; (xxi) 180-190; (xxii) 190-200; (xxiii) 200-210; (xxiv) 210-220; (xxv) 220-230; (xxvi) 230-240; (xxvii) 240-250; and (xxviii) >250.

According to less preferred embodiment the mass analyser may be selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a FouJtrier Transform electrostatic or orbitrap mass analyser; and (xi) a Fourier Transform mass analyser.

According to an embodiment the mass spectrometer preferably further comprises processing means wherein the processing means is arranged and adapted to filter mass spectral data obtained by the mass analyser so that a mass spectrum is produced comprising mass spectral data relating to: (i) ions having a single charge; (ii) ions having two charges; (iii) ions having three charges; (iv) ions having four charges; (v) ions having five charges; (vi) ions having more than five charges; and (vii) multiply charged ions.

According to another aspect of the present invention there is provided a method of mass spectrometry comprising:

separating ions in an ion mobility spectrometer or separator;

receiving ions from the ion mobility separator or spectrometer into a first ion guide arranged downstream of the ion mobility spectrometer or separator, the first ion guide comprising a plurality of electrodes;

applying one or more voltages or one or more voltage waveforms to the electrodes of the first ion guide so that in a first mode of operation ions received from the ion mobility spectrometer or separator are trapped and/or transported and/or translated in separate regions or portions of the first ion guide; and providing a mass analyser downstream of the first ion guide.

According to another aspect of the present invention there is provided a mass spectrometer comprising an ion guide arranged downstream of an ion mobility spectrometer or separator, wherein in use one or more transient DC voltages or potentials or one or more transient DC voltage or potential waveforms are applied to the ion guide in order to create a plurality of axial potential wells in the ion guide.

According to another aspect of the present invention there is provided a mass spectrometer comprising an ion guide arranged downstream of an ion mobility spectrometer or separator, wherein in use two or more phase-shifted AC or RF voltages are applied to the ion guide in order to create a plurality of axial potential wells in the ion guide.

According to another aspect of the present invention there is provided a mass spectrometer comprising an ion guide arranged downstream of an ion mobility spectrometer or separator, wherein in use a plurality of axial potential wells are created in the ion guide and/or are translated along the ion guide.

According to another aspect of the present invention there is provided a method of mass spectrometry comprising:

providing an ion guide downstream of an ion mobility spectrometer or separator; and applying one or more transient DC voltages or potentials or one or more transient DC voltage or potential waveforms to the ion guide in order to create a plurality of axial potential wells in the ion guide.

According to another aspect of the present invention there is provided a method of mass spectrometry comprising:

providing an ion guide arranged downstream of an ion mobility spectrometer or separator; and applying two or more phase-shifted AC or RF voltages to the ion guide in order to create a plurality of axial potential wells in the ion guide.

According to another aspect of the present invention there is provided a method of mass spectrometry comprising:

providing an ion guide arranged downstream of an ion mobility spectrometer or separator; and creating a plurality of axial potential wells in the ion guide and/or translating a plurality of axial potential wells along the ion guide.

The preferred embodiment relates to a mass spectrometer and a method of mass spectrometry wherein ions having certain specific charge states (e.g. multiply charged ions) can be separated from ions having other charge states (e.g. singly charged ions) using an ion mobility spectrometer or separator. The ions are then preferably passed to an ion guide in which a plurality of axial potential wells are created and which are then preferably translated along the length of the ion guide. The ion guide is preferably arranged and adapted to preserve the fidelity and composition of groups or packets of ions as they emerge from the ion mobility spectrometer or separator and as are received by the ion guide. The ion guide also preferably enables the sampling duty cycle of a Time of Flight mass analyser arranged downstream of the ion guide to be optimised.

A method of mass spectrometry according to a preferred embodiment of the present invention comprises: providing a pulse of ions and performing the following steps before providing another pulse of ions: (a) temporally separating at least some of the ions according to their ion mobility in an ion mobility spectrometer or separator; (b) collecting at least some of the ions which emerge from the ion mobility spectrometer or separator in an ion guide and partitioning the ions received in the ion guide into groups or packets with a series of potential hills or barriers separating each group of ions and wherein the ions are partitioned according to their arrival times at the exit of the ion mobility spectrometer or separator; (c) transporting the ions in the ion guide wherein the ions are confined radially by an inhomogeneous RF electric field and are propelled or urged forwards along the ion guide by the series of potential hills or barriers which move or are otherwise translated along the axis of the ion guide; and (d) recording the mass spectrum of ions in one or more groups or packets of ions which are propelled or urged forwards to the exit of the ion guide by one or more of the series of potential hills or barriers.

The mass spectrometer is preferably capable of recording the full or partial mass spectrum of a packet of ions. The mass spectrometer may, for example, comprise a Time of Flight mass analyser. An orthogonal acceleration Time of Flight mass analyser is particularly preferred. According to other embodiments the mass analyser may comprise a linear quadrupole ion trap mass analyser, a 3D quadrupole ion trap mass analyser, an orbitrap mass analyser, a Penning trap mass analyser or an ion cyclotron trap mass analyser. The mass analyser may comprise a variant of the aforementioned mass analysers employing Fourier Transforms of mass dependant resonance frequencies.

By recording the full or partial mass spectrum of the ions in each packet of ions transmitted by the ion guide any desired charge state present in a complex mixture of ions may be detected and then preferentially selected or displayed when generating a final mass spectrum. Mass spectral data relating to ions having undesired charge states may either not be recorded or may be removed or otherwise filtered so that such mass spectral data is not displayed in the final mass spectrum.

In a preferred embodiment the mass spectrometer comprises an orthogonal acceleration Time of Flight mass analyser. In a conventional Time of Flight mass spectrometer ions are arranged to possess approximately the same energy and are then passed to an orthogonal acceleration region adjacent a pusher electrode. An orthogonal acceleration electric field is periodically applied to the orthogonal acceleration region by energising the pusher electrode. The length of the orthogonal acceleration region, the energy of the ions and the frequency of the application of the orthogonal acceleration electric field will determine the sampling duty cycle of the ions. Ions having approximately the same energy but having different mass to charge ratios will have different velocities and hence will have different sampling duty cycles.

In contrast to conventional arrangements, according to the preferred embodiment ions are preferably released from an ion guide upstream of an orthogonal acceleration Time of Flight mass analyser. The ions are preferably released in a succession of packets from the ion guide wherein preferably all the ions in a packet of ions released from the ion guide will preferably have a relatively narrow range of mass to charge ratios and therefore velocities. As a result, substantially all the ions in a packet of ions released from the ion guide can be arranged so as to arrive at the orthogonal acceleration region of the Time of Flight mass analyser at a time when an orthogonal acceleration electric field is applied. As a result, a relatively high sampling duty cycle can be achieved for most or preferably all of the ions being ejected or released from the ion guide.

In order to achieve a relatively high sampling duty cycle it is desirable that each packet of ions is released from the ion guide such that the time for the ions contained in a packet of ions to arrive at the orthogonal acceleration region is sufficiently short such that the ions do not disperse in the axial direction to a greater extent than the width of the orthogonal acceleration region (which substantially corresponds with the width of the pusher electrode). Accordingly, the distance from the point of release of the ions from the ion guide to the orthogonal acceleration region of the Time of Flight mass analyser is preferably sufficiently short given the energy of the ions and the range of mass to charge ratios of the ions contained within each packet of ions. The range of mass to charge ratios of ions within each packet of ions translated along the ion guide is preferably arranged to be relatively narrow or small. The orthogonal acceleration electric field is preferably applied in synchronism with the arrival of the ions at the orthogonal acceleration region. According to the preferred embodiment it is possible to achieve a sampling duty cycle of substantially 100% for all the ions in a packet of ions released from the ion guide. Furthermore, if the optimum conditions apply for each and every packet of ions released from the ion guide, then an overall sampling duty cycle approaching 100% may be achieved according to the preferred embodiment.

The preferred embodiment preferably comprises an ion mobility spectrometer or separator which is preferably coupled to a mass analyser, preferably an orthogonal acceleration Time of Flight mass analyser via an intermediate ion guide. The preferred embodiment preferably enables ions to be separated according to their charge state and preferably enables a relatively high sampling duty cycle to be obtained for ions having a wide range of mass to charge ratios.

A particularly preferred aspect of the present invention is that an ion guide is preferably positioned or otherwise located between an ion mobility spectrometer or separator and a mass analyser. Ions are preferably transported in and along the ion guide by a succession of potential hills or barriers which are preferably created within the ion guide. As a result, a plurality of axial potential wells are preferably created in the ion guide which preferably move or are otherwise translated along the axis of the ion guide. The ion mobility spectrometer or separator and the ion guide are preferably sufficiently closely coupled such that ions emerging from the exit of the ion mobility spectrometer or separator are preferably received in successive axial potential wells created in the ion guide. According to the preferred embodiment the order or composition of the ions emerging from the exit of the ion mobility spectrometer or separator is preferably maintained or otherwise preserved as the ions become trapped in different or separate axial potential wells in the ion guide. An orthogonal acceleration Time of Flight mass analyser is preferably positioned downstream of the ion guide in order to mass analyse ions as they emerge or are released from the ion guide. The ion guide and the orthogonal acceleration Time of Flight mass analyser are also preferably sufficiently closely coupled such that each packet or group of ions released from the exit of the ion guide is then preferably sampled by the orthogonal acceleration Time of Flight mass analyser with a sampling duty cycle which may approach substantially 100% according to the preferred embodiment.

Ions passing through the preferred ion mobility spectrometer or separator are preferably subjected to an electric field in the presence of a buffer gas. Different species of ion will preferably acquire different velocities and will preferably become separated according to their ion mobility as they pass through the preferred ion mobility spectrometer or separator. The mobility of an ion in the ion mobility spectrometer or separator will preferably depend upon the size, shape and charge state of the ion. One form of ion mobility spectrometer or separator which may be used comprises a drift tube or cell wherein an axial electric field is applied along the length of the drift tube or cell and a relatively high pressure buffer gas is provided. Ions having relatively high ion mobilities will preferably pass faster through the ion mobility spectrometer or separator than ions having relatively lower ion mobilities. Ions are therefore preferably separated according to their ion mobility in the ion mobility spectrometer or separator. In one embodiment the drift tube or cell may also act as an ion guide in that ions are radially confined within the drift tube or cell by the application of an inhomogeneous RF field to electrodes forming the ion mobility spectrometer or separator. However, according to other embodiments ions may not be radially confined within the drift tube or cell.

According to a preferred embodiment the ion mobility spectrometer or separator preferably comprises a plurality of electrodes wherein ions are radially confined within the ion mobility spectrometer or separator by the application of an inhomogeneous RF electric field to the electrodes. The electrodes preferably comprise a plurality of electrodes having apertures through which ions are transmitted in use. Ions may be urged forwards through the ion mobility spectrometer or separator by one or more potential hills or one or more transient DC voltages or potentials which are preferably arranged to move along the axis of the preferred ion mobility spectrometer or separator in the presence of a buffer gas. Appropriate selection of the amplitude and velocity of the one or more potential hills or the one or more transient DC voltages or potentials and the type and pressure of the buffer gas can ensure that at least some ions are able to selectively slip or otherwise pass over the one or more potential hills or one or more transient DC voltages or potentials as they are translated forward. Ions will therefore preferably be differentially affected by the translation of the one or more potential hills in a manner dependent upon their ion mobility. As a result ions having different ion mobilities are preferably transported at different velocities through the ion mobility spectrometer or separator and become separated depending upon or according to their ion mobility.

The cycle time for separating a group of ions according to their ion mobility in the preferred ion mobility spectrometer or separator may be between 2 and 50 ms, preferably between 5 and 20 ms and further preferably about 10 ms. The cycle time for mass analysing a packet of ions using a Time of Flight mass analyser may be between 10 and 250 µs, preferably between 20 and 125 µs, and further preferably about 50 µs.

As an illustrative example only, ions may be separated according to their ion mobility in a preferred ion mobility spectrometer or separator over a time period of approximately 10 ms. The ions emerging from the preferred ion mobility spectrometer or separator may then be collected in one of 200 separate axial potential wells which are preferably successively created in the ion guide which are then preferably subsequently translated along the length of the ion guide. Ions emerging from an axial potential well as the axial potential well reaches the exit of the preferred ion guide may then be mass analysed in a time period of 50 µs. For each cycle of creating an axial potential well and translating the axial potential well along the length of the ion guide there is preferably also a corresponding cycle or orthogonal acceleration and mass analysis of ions by the Time of Flight mass analyser. According to the preferred embodiment the delay time between the release of a packet of ions from the ion guide and the subsequent application of an orthogonal acceleration voltage to a pusher electrode disposed adjacent the orthogonal acceleration region of the Time of Flight mass analyser is preferably progressively increased. The delay time is preferably increased since the average mass to charge ratio of ions released from successive potential wells as they reach the exit of the ion guide also preferably increases reflecting the fact that for ions having a particular charge state lower mass to charge ratio ions will emerge from the exit of the ion mobility spectrometer or separator prior to relatively higher mass to charge ratio ions.

An ion source is preferably arranged upstream of the preferred ion mobility spectrometer or separator and may comprise a pulsed ion source such as a Laser Desorption ionisation ("LDI") ion source, a Matrix Assisted Laser Desorption Ionisation ("MALDI") ion source or a Desorption Ionisation on Silicon ("DIOS") ion source. Alternatively, a continuous ion source may be used in which case an ion trap upstream of the preferred ion mobility spectrometer or separator may be provided. The ion trap is preferably arranged to store ions received from the ion source and periodically to release the ions into or towards the ion mobility spectrometer or separator. The continuous ion source may comprise an Electrospray Ionisation ("ESI") ion source, an Atmospheric Pressure Chemical Ionisation ("APCI") ion source, an Electron Impact ("EI") ion source, an Atmospheric Pressure Photon Ionisation ("APPI") ion source, a Chemical Ionisation ("CI") ion source, a Fast Atom Bombardment ("FAB") ion source, a Liquid Secondary Ion Mass Spectrometry ("LSIMS") ion source, a Field Ionisation ("FI") ion source or a Field Desorption ("FD") ion source. Other pulsed, continuous or pseudo-continuous ion sources may also be used. An Atmospheric Pressure ionisation ion source is particularly preferred.

The mass spectrometer may further comprise a mass filter or mass analyser preferably arranged downstream of the ion source and preferably arranged upstream of the preferred ion mobility spectrometer or separator. The mass filter or mass analyser may, for example, be used to transmit specific parent or precursor ions having a specific mass to charge ratio or having mass to charge ratios within a particular range to the preferred ion mobility spectrometer or separator. The mass filter may, for example, comprise a quadrupole rod set mass filter, a Time of Flight mass analyser, a Wein filter or a magnetic sector mass analyser.

The mass spectrometer may comprise a collision or fragmentation cell preferably arranged upstream of the preferred ion mobility spectrometer or separator. In one mode of operation at least some parent or precursor ions entering the collision or fragmentation cell may be caused to fragment. The resulting daughter, fragment or product ions are then preferably transmitted to the preferred ion mobility spectrometer or separator. The daughter, fragment or product ions are then preferably separated in the preferred ion mobility spectrometer or separator according to their ion mobility.

Although an orthogonal acceleration Time of Flight mass analyser is particularly preferred, according to other less preferred embodiments the mass spectrometer may comprise a quadrupole mass analyser, a 3D ion trap mass analyser, a linear ion trap mass analyser, a Fourier Transform Ion Cyclotron Resonance mass analyser, a Fourier Transform Orbitrap mass analyser or a magnetic sector mass analyser.

BRIEF DESCRIPTION OF THE DRAWINGS

Various embodiments of the present invention together with other arrangements given for illustrative purposes only will now be described, by way of example only, and with reference to the accompanying drawings in which:

FIG. 2A shows a portion of a mass spectrum obtained conventionally using normal detector gain and FIG. 2B shows a comparable mass spectrum obtained by lowering the detector gain;

FIG. 6 shows a first preferred embodiment of the present invention wherein an ion guide in which a plurality of axial potential wells are created is used to interface an ion mobility spectrometer or separator to an orthogonal acceleration Time of Flight mass analyser;

FIG. 13A shows a mass spectrum obtained conventionally and FIG. 13B shows a comparable mass spectrum obtained by enhancing the sampling duty cycle in a manner according to an embodiment of the present invention;

DETAIL DESCRIPTION OF THE PREFERRED EMBODIMENTS

Figure 1:
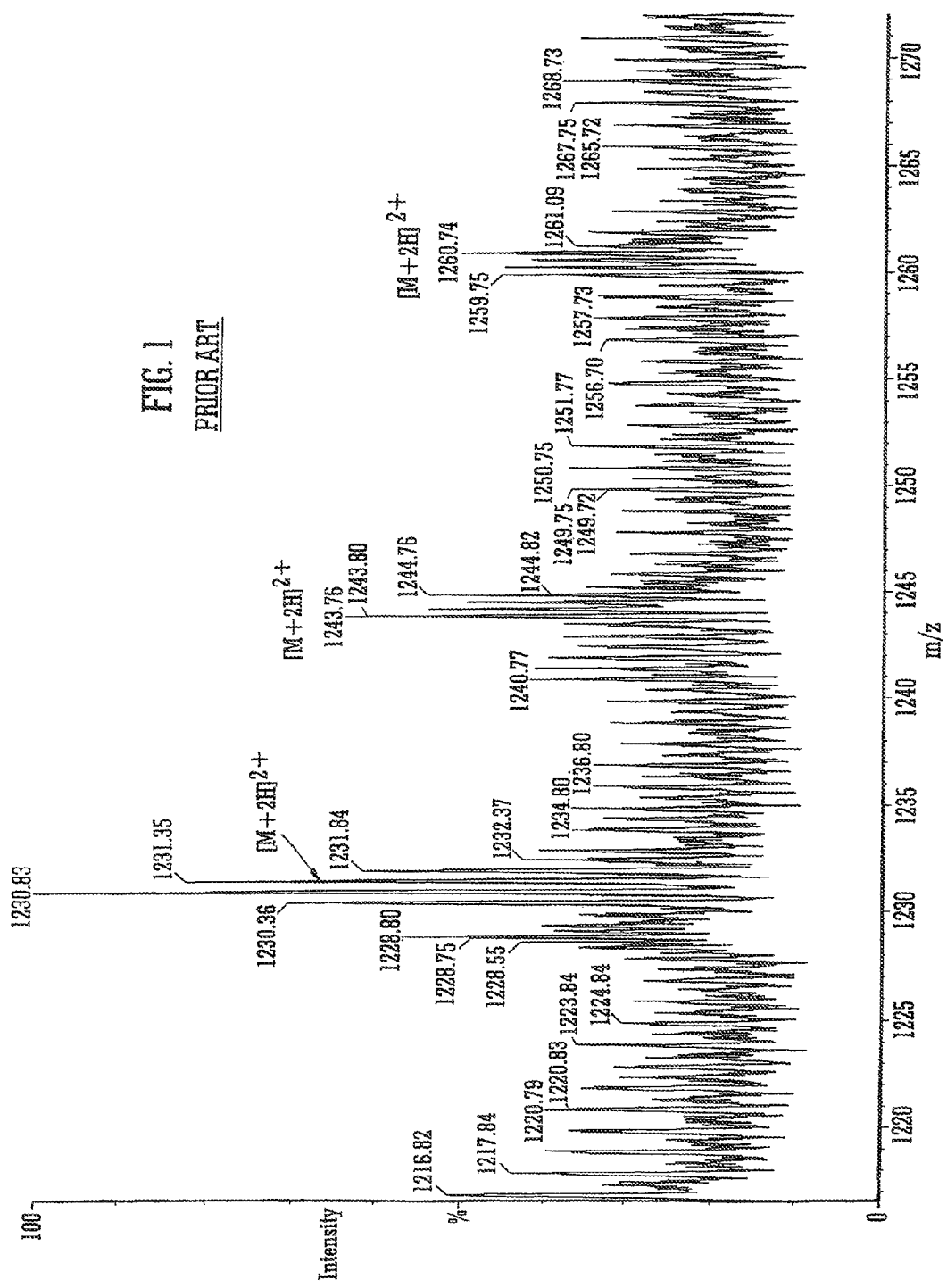
FIG. 1 shows a portion of a mass spectrum obtained conventionally wherein doubly charged analyte ions of interest are partially obscured amongst a background of singly charged ions.

FIG. 1 shows a typical mass spectrum obtained conventionally and illustrates how doubly charged analyte ions of potential interest may be relatively obscured amongst a background of singly charged ions. Being able effectively to filter out singly charged ions which relate to chemical noise so that the mass spectrometer can more easily target multiply charged peptide related ions would be particularly advantageous for the study of protein digests. Where chemical noise is not the limitation to detection then it would still nonetheless be advantageous to be able to increase the transmission and sampling efficiency of analyte ions of interest thereby improving the sensitivity of the mass spectrometer. As will be discussed, the preferred embodiment of the present invention advantageously enables chemical noise (e.g. singly charged ions) to be reduced or substantially removed from the final mass spectrum and the preferred embodiment also preferably enables the transmission and sampling duty cycle of analyte ions of interest to be increased. The preferred embodiment is therefore particularly advantageous in the study of protein digests.

For illustrative purposes only some conventional approaches to reducing the effect of singly charged background ions which may obscure multiply charged analyte ions of interest will now be discussed. It is know to operate an ion detector so as to favour the detection of multiply charged ions relative to singly charged ions. The ion detector of an orthogonal acceleration Time of Flight mass analyser may, for example, count the arrival of ions using a Time to Digital Converter ("TDC") which may have a certain discriminator threshold. The voltage pulse produced by a single ion arriving at the on detector must be high enough to exceed the voltage threshold thereby triggering the discriminator and so registering the arrival of an ion. The ion detector producing the voltage pulse may comprise an electron multiplier or a Microchannel plate ("MCP") detector. These detectors are charge sensitive so that the size of the signal they produce increases with increasing charge state of the ions detected. Discrimination in favour of higher charge states can therefore be accomplished by increasing the discriminator voltage level, lowering the detector gain, or by a combination of both approaches.

FIG. 2A shows a mass spectrum obtained conventionally with normal detector gain. FIG. 2B shows a comparable mass spectrum obtained by reducing the detector gain. It can be seen from FIGS. 2A and 2B that whilst reducing the detector gain (or increasing the discriminator level) discriminates in favour of multiply charged ions, a significant disadvantage of this approach is that the sensitivity is adversely lowered. As can be seen from the ordinate axes of FIGS. 2A and 2B, the sensitivity is reduced by a factor of about ×4 when a lower detector gain is employed. The approach of lowering the detector gain also does not make it possible to select ions having a particular charge state. Instead, the best that can be achieved is a reduction of the efficiency of detection of lower charge states with respect to higher charge states.

An alternative approach to being able to preferentially select ions having a particular charge state is made possible by coupling an ion mobility spectrometer or separator to a Time of Flight mass analyser.

Ions in an ion mobility spectrometer or separator are subjected to an electric field in the presence of a buffer gas. Different species of ion will acquire different velocities and will become temporally separated according to their ion mobility as they pass through the ion mobility spectrometer or separator. The mobility of an ion in such an ion mobility spectrometer or separator will depend upon the size, shape and charge state of the ion. Relatively large ions with one charge will normally have relatively lower mobilities than relatively small ions having a single charge. Also, ion having one charge will also normally have a lower ion mobility than an ion relating to the same compound but which has two charges.

One form of an ion mobility separator or spectrometer comprises a drift tube or cell along which an axial electric field is maintained. A relatively high pressure buffer gas is maintained within the drift tube or cell. The combination of an axial electric field and the relatively high pressure background gas causes ions having a relatively high ion mobility to pass more quickly through the drift tube or cell compared to ions having a relatively low ion mobility. Ions are therefore caused to separate according to their ion mobility.

The ion mobility separator or spectrometer may operate at or around atmospheric pressure. Alternatively, the ion mobility separator or spectrometer may operate under a partial vacuum at a pressure down to as low as about 0.01 mbar. The ion mobility spectrometer or separator may comprise a plurality of electrodes having apertures through which ions are transmitted in use. A DC voltage gradient may be maintained across at least a portion of the ion mobility spectrometer or separator and at least some of the electrodes may be connected to an AC or RF voltage supply. The frequency of the AC or RF voltage is typically in the range 0.1-3.0 MHz. This form of ion mobility spectrometer or separator is particularly advantageous in that the AC or RF voltage applied to the electrodes causes a pseudo-potential well to be created which acts to confine ions radially within the ion mobility spectrometer or separator. Radial confinement of the ions will result in higher ion transmission compared with an ion mobility separator or spectrometer which does not confine ions radially.

In another form of ion mobility spectrometer or separator ions are confined radially by an inhomogeneous RF field. Ions are urged forwards through the ion mobility spectrometer or separator by a series of relatively low amplitude potential hills that move along the axis of the ion mobility spectrometer or separator. A relatively high pressure buffer gas is maintained within the ion mobility spectrometer or separator. Appropriate selection of the amplitude and velocity of the plurality of potential hills together with appropriate selection of the type and pressure of the buffer gas allows ions to selectively slip or pass over the relatively low amplitude potential hills in a manner which is dependent upon the mobility of the ions. Accordingly, ions of different mobility will be transported at different velocities through the ion mobility spectrometer or separator and will therefore become temporally separated according to their ion mobility.

By providing a Time of Flight mass analyser downstream of the ion mobility spectrometer or separator to receive ions emerging from the ion mobility spectrometer or separator it is possible to detect and record only those ions having certain desired charge states. Alternatively, mass spectral data relating to all ions may be obtained but the mass spectral data may then be post-processed so as to filter out mass spectral data relating to ions having undesired charge states. The final mass spectrum can therefore be arranged to display only ions having certain desired charged states.

Figure 3A:
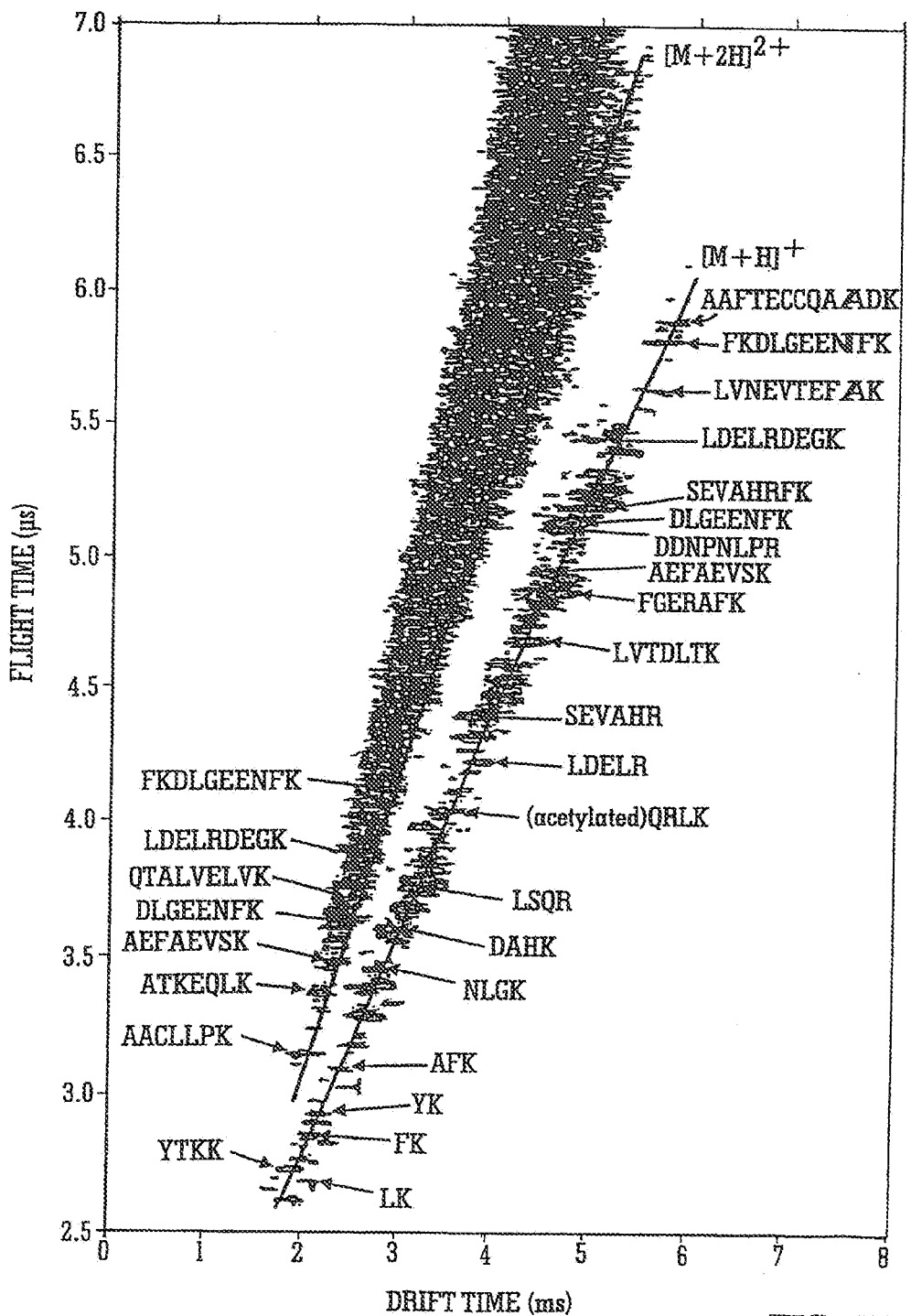
FIG. 3A illustrates the known relationship between the drift time of ions through an ion mobility spectrometer or separator and the subsequent time of flight of the ions (which is directly related to the mass to charge ratio of the ion) in a Time of Flight mass analyser drift region for various singly and doubly charged ions and FIG. 3B shows an experimentally determined relationship between the drift time of a mixture of singly and doubly charged ions through an ion mobility spectrometer or separator and their mass to charge ratio.

The combination of an ion mobility spectrometer or separator and a Time of Flight mass analyser may advantageously be used, for example, to generate a mass spectrum relating just to doubly charged ions from a tryptic digest of a large protein. Ions of differing mobility will be separated in the ion mobility spectrometer or separator and will have different drift times. The orthogonal acceleration Time of Flight mass analyser then effectively provides a further separation of the ions according to their mass to charge ratio. A resulting two dimensional plot of flight time through the mass analyser against drift time through the ion mobility spectrometer or separator can be generated. An example of such a two dimensional plot is shown in FIG. 3A. It can be seen from FIG. 3A that singly charged $[M+H]^+$ ions lie on a certain characteristic line which is different to that of doubly charged $[M+2H]^{2+}$ ions. Accordingly, the Time of Flight mass analyser can be used just to record the flight time just of ions having a desired mass to charge ratio. Alternatively, the Time of Flight mass analyser may be used to record the flight times of all ions having all mass to charge ratios and charge states. The resulting mass spectral data may then be post-processed to select and present a mass spectrum relating just to ions having certain specific desired charge states.

Figure 3B:
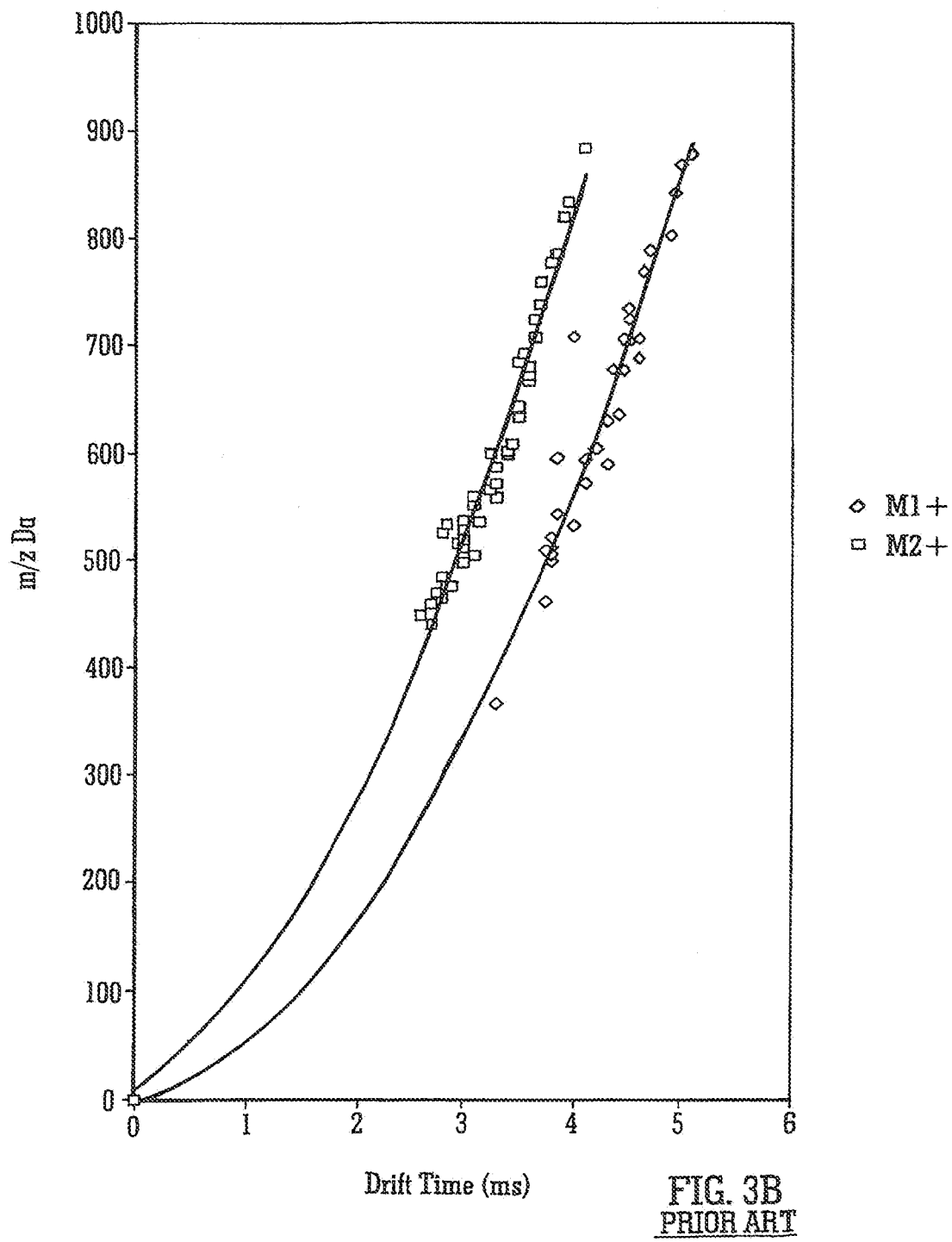

A further experimentally determined relationship between the mass to charge ratio of ions and their drift time through an ion mobility spectrometer or separator is shown in FIG. 3B. As can be seen from FIGS. 3A and 3B, a doubly charged ion having the same mass to charge ratio as a singly charged ion will take less time to drift through the ion mobility spectrometer or separator compared with a singly charged ion. Although the ordinate axis of FIG. 3A is given as the flight time through the flight region of a Time of Flight mass analyser, it will be appreciated that this correlates directly with the mass to charge ratio of the ion.

Figure 4A:
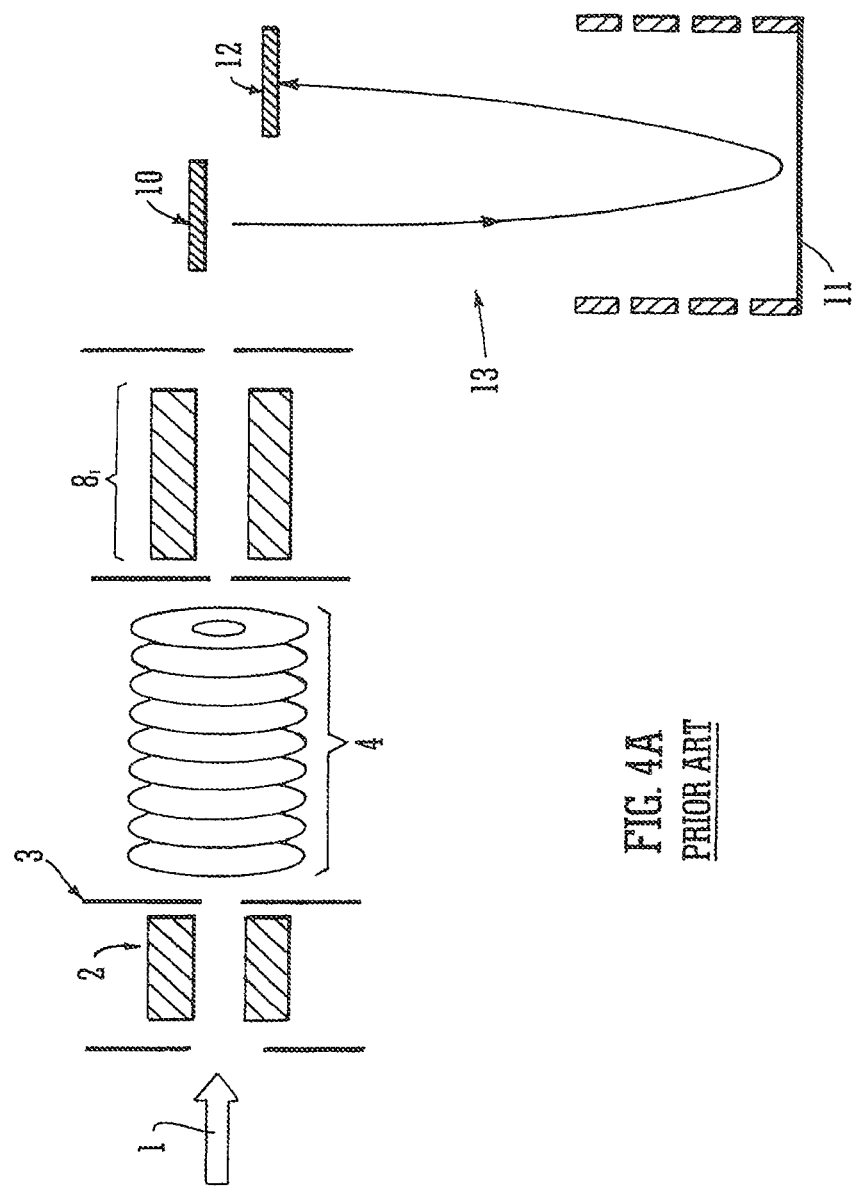
FIG. 4A shows a conventional mass spectrometer comprising an ion mobility spectrometer or separator coupled to a Time of Flight mass analyser via a transfer lens and FIG. 4B illustrates how a first packet of ions may be gated into an ion mobility spectrometer or separator and the ions emerging from the ion mobility spectrometer or separator are then repeatedly pulsed into the drift region of an orthogonal acceleration Time of Flight mass analyser before a second packet of ions is gated into the ion mobility spectrometer or separator.

A known mass spectrometer is shown in FIG. 4A. According to this arrangement ions 1 emitted from an Electrospray ion source are stored in an ion trap 2. The ions are then released periodically (at time T=0) from the ion trap 2 via a gate electrode 3. The ions then pass into the drift cell of an ion mobility spectrometer or separator 4. As will be apparent from FIGS. 3A and 3B, the typical drift time of ions through the ion mobility spectrometer or separator 4 is of the order of a few milli-seconds (ms).

After all the ions which were initially pulsed into the ion mobility spectrometer or separator 4 have traversed the length of the ion mobility spectrometer or separator 4, a new pulse of ions is ejected from the ion trap 2 and is admitted into the ion mobility spectrometer or separator 4. The process of separating ions in the ion mobility spectrometer or separator 4 according to their ion mobility is then repeated.

The time taken for an ion to exit the ion mobility spectrometer or separator 4 and arrive at the pusher electrode 10 of the Time of Flight mass analyser 13 which is arranged downstream of the ion mobility spectrometer or separator 4 is a function of the ion mobility of the ion. Ions having a relatively high ion mobility will take a relatively short time to transverse the ion mobility spectrometer or separator 4 and reach the orthogonal acceleration region adjacent the pusher electrode 10 of the Time of Flight mass analyser. Synchronisation of the energisation of the pusher electrode 10 with that of the gate electrode 3 at the entrance to the ion mobility spectrometer or separator 4 enables the combination of the ion mobility spectrometer or separator 4 and the Time of Flight mass analyser 13 to be used such that it is possible to discriminate or select mass spectral data relating to ions having a particular charge state.

Figure 4B:
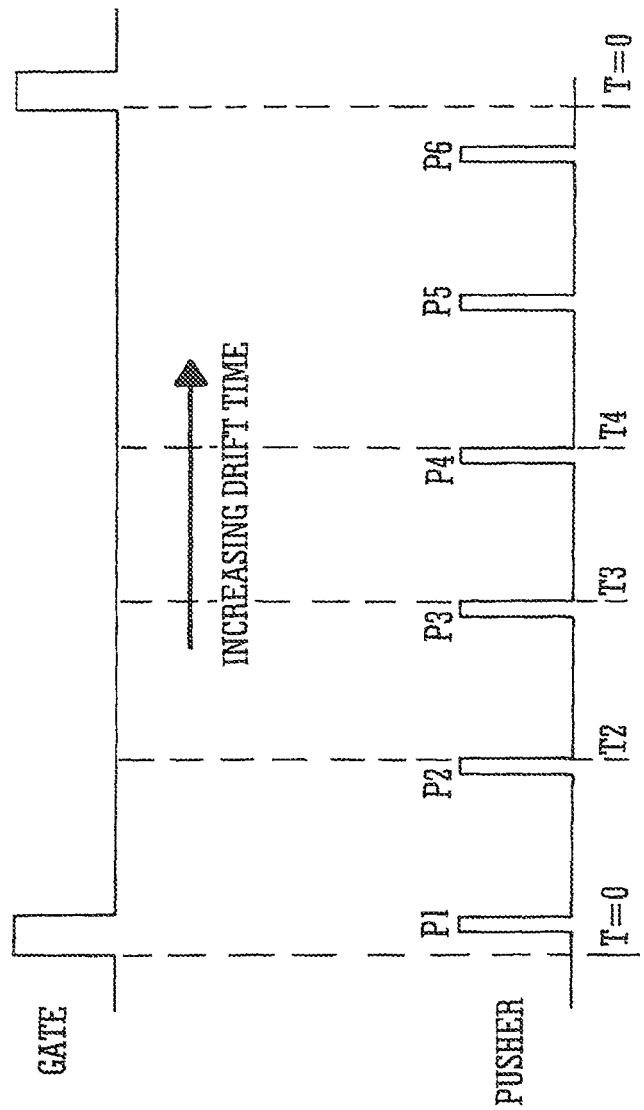

FIG. 4B shows how a series of pusher pulses ($P_1$ to $P_6$) or energisations of a pusher electrode 10 of a Time of Flight mass analyser 13 may be effected within or during one cycle of ions being pulsed into an ion mobility spectrometer or separator 4. Six pulses are shown in FIG. 4B for ease of illustration only. However, in practice, the pusher electrode 10 may be energised, for example, several hundred times before a new pulse of ions is admitted into the ion mobility spectrometer or separator 4. Ions arriving at the ion detector 12 due to being orthogonally accelerated by the first pusher pulse $P_1$ will have a slightly higher ion mobility than the ions subsequently orthogonally accelerated by the second pusher pulse $P_2$. Similarly, ions which are orthogonally accelerated by pusher pulse $P_n$ will have a slightly higher ion mobility than ions orthogonally accelerated by pusher pulse $P_{n+1}$. Summing all of the mass spectral data due to all the pusher pushes during a single cycle of ions being pulsed into the ion mobility spectrometer or separator 4 enables an integrated mass spectrum to be produced which corresponds to ions having all charge states and mobilities. Each individual mass spectrum acquired due to a single pusher pulse event $P_n$ can be considered as relating to a vertical section or slice through the plot show in FIG. 3B at a particular drift time $T_n$ (where $T_n$ is defined as the time between ions being pulsed into the on mobility spectrometer or separator 4 and the application of pusher pulse $P_n$).

If the Time of Flight, acquisition for a particular pusher pulse $P_n$ is configured such that experimental data is either only acquired or is only displayed relating to ions which arrive after a predetermined flight time, and the predetermined flight time is set so as to lie, for example, between the singly charged and doubly charged bands or regions as shown in FIG. 3B, then the resultant mass spectrum will then only relate to multiply charged ions. Mass spectral data relating to singly charged background ions is either not recorded or alternatively is excluded from the final mass spectrum which is displayed or otherwise generated.

The preferred value for the flight time cut-off may vary (e.g. increase) from pusher pulse $P_n$ to pusher pulse $P_{n+1}$. According to an embodiment all the mass spectral data from all the pushes in a single cycle of ions being pulsed into the ion mobility spectrometer or separator 4 may, for example, give a resultant integrated mass spectrum relating only to multiply charged ions. Mass spectral data relating to singly charged ions may be effectively eliminated or otherwise absent from the final mass spectrum.

Figure 5:
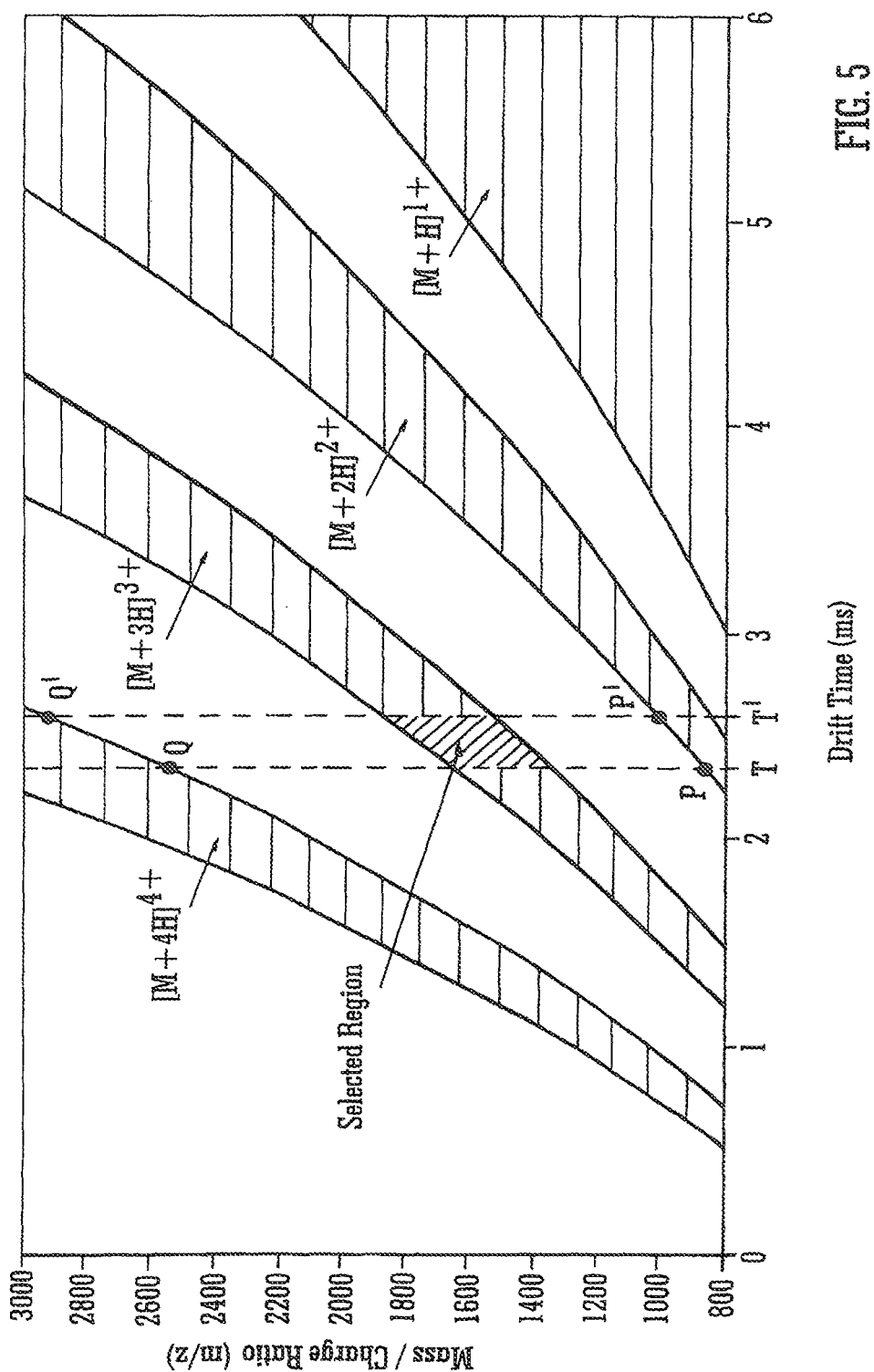
FIG. 5 illustrates the general principle of how ions having a certain charge state may be recognised or selected from mass spectral data obtained by coupling an ion mobility spectrometer or separator to a Time of Flight mass analyser.

Ions having specific charge state or range of charge states may be enhanced or alternatively attenuated by using the combination of both a low time of flight cut-off and a high time of flight cut-off. FIG. 5 illustrates how, for example, triply charged ions have an even shorter drift time through an ion mobility spectrometer or separator than doubly charged ions having the same mass to charge ratio. An upper flight time cut-off Q-Q' may be used in conjunction with a lower flight time cut-off P-P' so that only mass spectral relating to triply charged ions is either recorded or is used to generate the final mass spectrum.

According to an embodiment mass spectral data relating to all ions may be acquired but those ions having flight times below a lower time of flight cut-off for each pusher pulse $P_n$ may be discarded or excluded. Summation of all the mass spectral data from all pusher pushes can then be arranged to result in an integrated mass spectrum which relates just to multiply charged ions. The mass spectral data obtained may also be post-processed so as to select parts of each mass spectral data set between a lower time of flight cut-off and an upper time of flight cut-off. In this way it is possible to construct a mass spectrum relating to ions having, for example, just one specific charge state (e.g. doubly charged ions) or range of charge states (e.g. doubly ad triply charged ions). Indeed, according to an embodiment separate mass spectra may be constructed or otherwise presented for each separate charge state.

Another (unillustrated) method of preferentially selecting ions having a specific charge state in the presence of ions having other charge states is to separate the ions according to their ion mobility in an ion mobility spectrometer or separator. The ions emerging from the ion mobility spectrometer or separator are then passed to a mass filter. The mass filter may comprise, for example, a quadrupole rod set mass filter or an axial Time of Flight drift region in conjunction with a synchronised pusher electrode. The ions are then mass filtered according to their mass to charge ratio by the mass filter. A mass filtering characteristic (e.g. low mass to charge ratio cut-off) of the mass filter is progressively varied (e.g. increased) or stepped such that ions having a first charge state are onwardly transmitted whereas ions having a second different charge state are substantially attenuated by the mass filter. This allows ions having one or more certain specific charge states to be physically selected from a mixture of ions having differing charge states whilst ions having undesired charge states are physically attenuated by the mass filter. Multiply charged ions may be preferentially selected and onwardly transmitted by the mass filter whilst singly charged ions may be reduced or substantially attenuated by the mass filter. Alternatively, ions having two or more multiply charged states may, for example, be cowardly transmitted by the mass filter.

The mass filter may be operated as a high pass mass to charge ratio filter so as to transmit substantially only ions having a mass to charge ratio greater than a minimum mass to charge ratio. In this mode of operation multiply charged ions can be preferentially transmitted relative to singly charged ions i.e. doubly, triply, quadruply and ions having five or more charges may be onwardly transmitted by the mass filter whilst singly charged ions may be substantially attenuated by the mass filter.

Alternatively, the mass filter may be operated as a band pass mass to charge ratio filter so as to substantially transmit only ions having a mass to charge ratio greater than a minimum mass to charge ratio and less than a maximum mass to charge ratio. In this mode of operation multiply charged ions of a single charge state (e.g. triply charged) may be preferentially cowardly transmitted by the mass filter whilst ions having other charge states may be substantially attenuated by the mass filter. Alternatively, ions having two or more neighbouring or sequential charge states (e.g. doubly and triply charged ions) may be onwardly transmitted by the mass filter whilst ions having all other charge states may be substantially attenuated by the mass filter.

The mass filter may be scanned so that, for example, the minimum mass to charge ratio cut-off or the mass to charge ratio transmission window is progressively increased during a cycle of ions being pulsed into the ion mobility spectrometer or separator and emerging therefrom. The transmitted ions may then, for example, be recorded by a mass analyser such as an orthogonal acceleration Time of Flight mass analyser.

According to a less preferred arrangement, the mass filter may alternatively comprise a drift region which is maintained at a relatively low pressure. The drift region may have an axis and an injection electrode for injecting at least some ions in a direction substantially orthogonal to the axis. The injection electrode may comprise a pusher and/or puller electrode of an orthogonal acceleration Time of Flight mass analyser.

Another arrangement is contemplated wherein a second ion trap is positioned downstream of an ion mobility spectrometer or separator and upstream of a drift region. The second ion trap is arranged to store ions received from the ion mobility spectrometer or separator and then periodically to release ions so that a packet of ions is pulsed into the drift region. An injection electrode may be arranged to inject ions a predetermined period of time after ions have first been released from the second ion trap. The period of time may be set such that only ions having a desired mass to charge ratio or ions having mass to charge ratios within a desired range are injected by the injection electrode into an orthogonal acceleration Time of Flight mass analyser.

The latter arrangement also provides a mode of operation that offers a means of increasing sensitivity. Being able to increase the sensitivity is particularly advantageous even if singly charged background ions do not imposes a limit to the detection of analyte ions of interest.

In this mode of operation a first packet of ions may be released from the second ion trap and the timing of the orthogonal injection pulse may be set to a predetermined time delay. Then a second packet of ions may be released from the second ion trap and the predetermined time delay may be slightly increased. The process of increasing the time delay may be repeated a number of times during one cycle of pulsing ions into the ion mobility spectrometer or separator. The time delay may be increased as a function of the mass to charge ratio of the ions arriving at the exit of the ion mobility spectrometer or separator. By appropriate selection of the time delay function, the timing of the orthogonal injection may be optimised according to the mass to charge ratio of ions within each packet released into the drift region thereby optimising sensitivity.

The resolution or selectivity of an axial time of flight mass filter and the synchronised orthogonal injection of ions will depend upon the length of the drift region and the width of the orthogonal acceleration region. The longer the drift region, and the shorter the width of the orthogonal acceleration region then the greater the resolution or selectivity of the axial time of flight mass filter. However, the greater the resolution or selectivity of the axial time of flight mass filter the smaller the range of mass to charge ratios of ions which can be injected into the orthogonal acceleration Time of Flight mass analyser. If this range of mass to charge ratios is smaller than that present in the second ion trap then those outside that range of mass to charge ratios will be discarded. There can therefore be a conflict between the desire to discard as few ions as possible and whilst achieving adequate resolution or selectivity of the axial time of flight mass filter. The more selective the mass filter is, the more ions are likely to be discarded, thereby reducing any gain in sensitivity.

FIG. 6 shows a first embodiment of the present invention wherein an ion guide 6 is provided downstream of an ion mobility spectrometer or separator 4 and which effectively interfaces the ion mobility spectrometer or separator 4 to an orthogonal acceleration. Time of Flight mass analyser 13. A continuous ion source such as an Electrospray ion source may be provided and which generates a beam of ions 1. The beam of ions 1 is then preferably passed to an ion trap 2 which is preferably arranged upstream of the ion mobility spectrometer or separator 4. Ions are preferably pulsed out of the ion trap 2 by the application of an extraction voltage to an ion gate 3 which is preferably located or arranged at the exit of the ion trap 2. The ion gate 3 is also preferably arranged upstream of the ion mobility spectrometer or separator 4. The application of an extraction voltage to the ion gate 3 preferably causes a pulse of ions to be ejected out of the ion trap 2 and to pass into the ion mobility spectrometer or separator 4.

The ion trap 2 may comprise a quadrupole or other multipole rod set. According to a preferred embodiment the ion trap 2 may have a length of approximately 75 mm. According to other embodiments the ion trap 2 may comprise an ion tunnel ion trap comprising a plurality of electrodes having apertures through which ions are transmitted in use. The apertures are preferably all the same size. In other embodiments at least 60%, 65%, 70%, 75%, 80%, 85%, 90% or 95% of the electrodes of the ion trap 2 have apertures which are substantially the same size. The ion trap 2 may according to one embodiment comprise approximately 50 electrodes having apertures through which ions are transmitted.

Adjacent electrodes of the ion trap 2 are preferably connected to opposite phases of a two phase AC or RF voltage supply. The application of a two phase AC or RF voltage to the electrodes of the ion trap 2 preferably causes ions to be radially confined, in use, within the ion trap 2 due to the generation of a radial pseudo-potential well. The AC or RF voltage applied to the electrodes of the ion trap 2 may have a frequency within the range 0.1-3.0 MHz, preferably 0.3-2.0 MHz, further preferably 0.5-1.5 MHz.

Figure 7A:
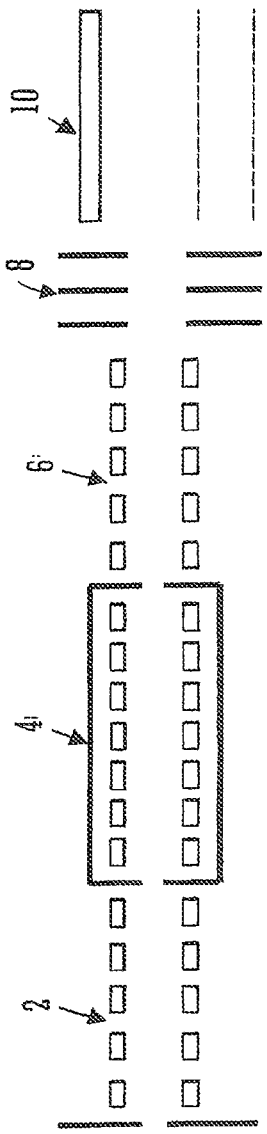
FIG. 7A shows an embodiment of the present invention wherein an ion trap is arranged upstream of an ion mobility spectrometer or separator in order to pulse ions into the ion mobility spectrometer or separator and an ion guide in which a plurality of axial potential wells are created is provided downstream at the ion mobility spectrometer or separator and upstream of a Time of Flight mass analyser.
Figure 7B:
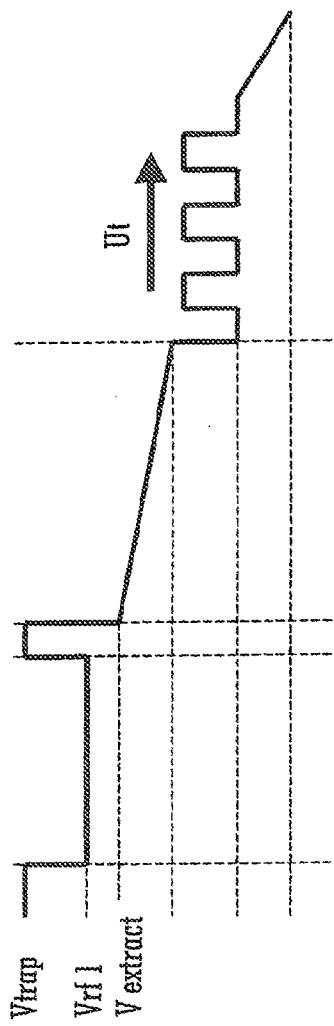
FIG. 7B shows the potential profile for an ion trap, ion mobility spectrometer or separator and an ion guide according to an embodiment of the present invention wherein a trapping DC voltage is applied to the ion trap, a constant DC voltage gradient is maintained across the ion mobility spectrometer or separator and a plurality of axial potential wells are formed in the ion guide which are then translated towards the exit of the ion guide

In a preferred embodiment the electrodes comprising the ion trap 2 are preferably maintained at a certain DC voltage $V_{rf1}$ (as shown in FIG. 7B). In order to trap ions within the ion trap 2, the ion gate 3 arranged downstream of the ion trap 2 is preferably maintained at a higher DC potential $V_{trap}$ than the DC potential $V_{rf1}$ at which the electrodes of the ion trap 2 are maintained. Accordingly, ions are preferably confined axially within the ion trap 2 and are preferably substantially prevented from leaving the ion trap 2. The voltage applied to the ion gate 3 is then preferably periodically dropped to a potential $V_{extract}$ which is preferably lower than the potential $V_{rf1}$ at which the electrodes of the ion trap 2 are otherwise normally maintained. The potential is only dropped to the relatively low potential $V_{extract}$ for a relatively short period of time and this preferably causes a pulse of ions to be ejected out from the ion trap 2 and to be admitted or otherwise pass into the ion mobility spectrometer or separator 4 which is preferably arranged downstream of the ion trap 2.

According to an alternative embodiment a pulsed ion source may be used instead of a continuous ion source. The pulsed ion source may, for example, comprise a Matrix Assisted Laser Desorption Ionisation ("MALDI") ion source or a Laser Desorption Ionisation ion source. If a pulsed ion source is used then the ion source may be directly coupled to the ion mobility spectrometer or separator 4 in which case the ion trap 2 and ion gate 3 are not required and hence may be omitted.

The ion mobility spectrometer or separator 4 is preferably arranged such that ions which are pulsed into the ion mobility spectrometer or separator 4 are preferably caused to become temporally separated based upon or according to their ion mobility. The ion mobility spectrometer or separator 4 may take a number of different forms.

According to one embodiment the ion mobility spectrometer or separator 4 may comprise a drift tube having a number of guard rings distributed within the drift tube. The guard rings may be interconnected by equivalent valued resistors and connected to a DC voltage source. A linear or stepped DC voltage gradient may preferably maintained along the length of the drift tube. The guard rings are preferably not connected to an AC or RF voltage source according to this embodiment.

According to another embodiment the ion mobility spectrometer or separator 4 may comprise a plurality of ring, annular, plate or other electrodes. Each electrode preferably has an aperture therein through which ions are preferably transmitted in use. The apertures are preferably all the same size and are preferably circular. In other embodiments at least 50%, 55%, 60%, 65%, 70%, 75%, 80%, 85%, 90% or 95% of the electrodes of the ion mobility spectrometer or separator 4 have apertures which are substantially the same size or area.

According to the preferred embodiment the ion mobility spectrometer or separator 4 preferably has a length between 100 mm and 200 mm.

The ion mobility spectrometer or separator 4 preferably comprises a plurality of electrodes arranged in a vacuum chamber. The ion mobility separator or spectrometer 4 is preferably provided in a vacuum chamber which is preferably maintained, in use, at a pressure within the range 0.1-10 mbar. According to less preferred embodiments, the vacuum chamber may be maintained at pressures greater than 10 mbar and up to or near atmospheric pressure. According to other less preferred embodiments, the vacuum chamber may be maintained at pressures below 0.1 mbar.

Alternate or adjacent electrodes of the ion mobility spectrometer or separator 4 are preferably coupled to opposite phases of a two phase AC or RF voltage supply. The AC or RF voltage supply preferably has a frequency within the range 0.1-3.0 MHz, preferably 0.3-2.0 MHz, further preferably 0.5-1.5 MHz. The two phase AC or RF voltage preferably applied to the electrodes of the ion mobility spectrometer or separator 4 preferably causes a pseudo-potential well to be generated which preferably acts to radially confine ions within the ion mobility spectrometer or separator 4.

The electrodes comprising the ion trap 2 and the electrodes comprising the ion mobility spectrometer or separator 4 may according to one embodiment be interconnected by resistors to a DC voltage supply which may comprise a 400 V supply. The resistors which interconnect the electrodes of the ion mobility spectrometer or separator 4 may be substantially equal in value such that a substantially constant or linear axial DC voltage gradient may be maintained along the length of the ion mobility spectrometer or separator 4. FIG. 7B shows a linear DC voltage gradient being maintained across or along the ion mobility spectrometer or separator 4 according to this embodiment. However, according to other embodiments the DC voltage gradient maintained along the length of the ion mobility spectrometer or separator 4 may be slightly or substantially stepped in profile or may have a different profile.

The DC trapping potential or voltage $V_{trap}$ and the extraction potential or voltage $V_{extract}$ which are preferably applied to the ion gate 3 (if provided) may float on the DC voltage supply which is preferably connected to or applied to the ion mobility spectrometer or separator 4. The AC or RF voltage supply which is preferably applied to the electrodes of the on mobility spectrometer or separator 4 is preferably isolated from the DC voltage supply by a capacitor.

Figure 7C:
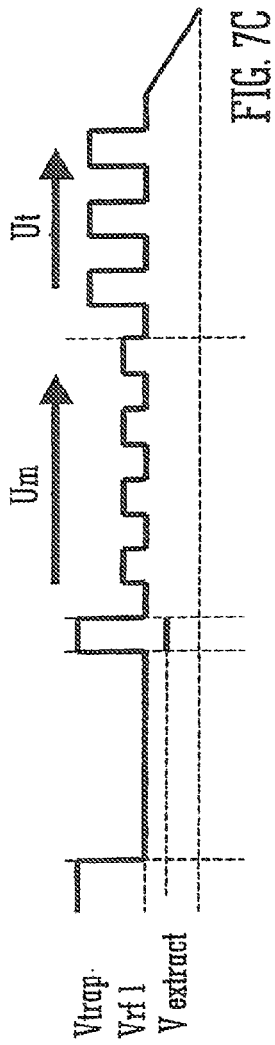
FIG. 7C shows the potential profile for an ion trap, ion mobility spectrometer or separator and an ion guide according to an embodiment of the present invention wherein a plurality of relatively low amplitude transient DC potentials are applied to the electrodes of the ion mobility spectrometer or separator in order to separate ions according to their ion mobility.

According to an alternative embodiment, the ion mobility spectrometer or separator 4 may comprise a plurality of electrodes having apertures through which ions are transmitted in use and wherein one or more transient DC voltages or one or more transient DC voltage waveforms are applied to the electrodes. The one or more transient DC voltages or one or more transient DC voltage waveforms which are preferably applied to the plurality of electrodes of the ion mobility spectrometer or separator 4 preferably form one or more potential hills which preferably have a relatively low amplitude such that at least some ions may pass or slip over the one or more potential hills as they are being translated along the length of the ion mobility spectrometer or separator 4. FIG. 7C illustrates this embodiment and shows a plurality of transient DC voltages having relatively low amplitudes being applied to the electrodes of the ion mobility spectrometer or separator 4. The one or more transient DC voltages or one or more transient DC voltage waveforms which are preferably applied to the electrodes of the ion mobility spectrometer or separator 4 are preferably progressively applied to a succession of electrodes forming the ion mobility spectrometer or separator 4 such that one or more potential hills move along the axis or length of the ion mobility spectrometer or separator 4 preferably towards the exit of the ion mobility spectrometer or separator 4.

A buffer gas is preferably maintained within the ion mobility spectrometer or separator 4 and preferably imposes a viscous drag upon the movement of ions. The amplitude and average velocity of the one or more potential hills which are preferably translated along the length of the ion mobility spectrometer or separator 4 is preferably set or is otherwise arranged such that at least some ions will slip or pass over a potential hill or barrier as it passes along the length of the ion mobility spectrometer or separator 4. Ions having relatively low ion mobilities are more likely to slip over a potential hill than ions having relatively high mobilities. As a result, ions having different ion mobilities will be transported at different velocities through and along the ion mobility spectrometer or separator 4. Ions will therefore become substantially separated according to their ion mobility.

Typical drift or transit times of ions through the preferred ion mobility spectrometer or separator 4 are of the order of a several milliseconds. After all the ions which were initially pulsed into the ion mobility spectrometer or separator 4 have preferably traversed the length of the ion mobility spectrometer or separator 4, another pulse of ions is preferably admitted or otherwise injected into the ion mobility spectrometer or separator 4. This marks the start of a new cycle of operation. Many cycles of operation may be performed during a single experimental run or analysis.

According to the preferred embodiment a particularly preferred aspect of the present invention is that an ion guide 6 is provided downstream of the ion mobility spectrometer or separator 4. The ion guide 6 may be provided in a separate vacuum chamber to that in which the ion mobility spectrometer or separator 4 is provided. Alternatively, the ion guide 6 may be provided in the same vacuum chamber as the ion mobility spectrometer or separator 4. If the ion guide 6 is provided in a separate vacuum chamber to that, of the ion mobility spectrometer or separator 4 then the two vacuum chambers are preferably separated by a differential pumping aperture 5 as shown in FIG. 6.

According to the preferred embodiment the ion guide 6 arranged downstream of the ion mobility spectrometer or separator 4 preferably comprises an ion guide comprising a plurality of plate, ring or annular electrodes having apertures through which ions are transmitted in use. The apertures of the electrodes forming the ion guide 6 are preferably all the same size. In less preferred embodiments at least 60%, 65%, 70%, 75%, 80%, 85%, 90% or 95% of the electrodes forming the ion guide 6 have apertures which are substantially the same size. Adjacent electrodes of the ion guide 6 are preferably connected to the opposite phases of a two phase AC or RF supply.

One or more transient DC voltages or one or more transient DC voltage waveforms are preferably applied to the plurality of electrodes forming the ion guide 6. As a result, one or more potential hills or barriers or axial potential wells are preferably formed in the ion guide 6 and which are then preferably translated along the length of the ion guide 6. The one or more transient DC voltages or one or more transient DC voltage waveforms are preferably progressively applied to a succession of electrodes of the ion guide 6 such that one or more potential hills or barriers or axial potential wells are created which preferably move along the axis of the ion guide 6 preferably towards the exit of the ion guide 6.

The one or more transient DC voltages or potentials or one or more transient DC voltage or potential waveforms which are preferably applied to the electrodes of the ion guide 6 preferably cause a plurality of axial potential wells to be created which are then preferably translated along the length of the ion guide 6. The one or more transient DC voltages or potentials or one or more transient DC voltage or potential waveforms which are preferably applied to the electrodes of the ion guide 6 preferably cause ions which emerge from the ion mobility spectrometer or separator 4 and which are received by or into the ion guide 6 to be partitioned or separated into a plurality of separate or discrete axial potential wells. The ions in each separate potential well are then preferably urged along and through the ion guide 6. The axial potential wells are preferably real potential wells rather than pseudo-potential wells.

The ion guide 6 is preferably provided in a vacuum chamber or is otherwise preferably maintained, in use, at a pressure within the range $10^{-3}$-$10^{-2}$ mbar. The ion guide 6 may preferably be maintained at a pressure which is at least on order of magnitude lower than the pressure at which the ion mobility spectrometer or separator 4 is maintained. According to less preferred embodiments the vacuum chamber in which the ion guide 6 is housed may be maintained at a pressure greater than $10^{-2}$ mbar up to a pressure at or near 1 mbar. According to less preferred embodiments, the vacuum chamber housing the ion guide 6 may alternatively be maintained at a pressure below $10^{-2}$ mbar. The gas pressure in the ion guide 6 is preferably sufficient to impose collisional damping of ion motion but is preferably not sufficient so as to impose excessive viscous drag upon the movement of ions.

The amplitude and average velocity of the one or more potential hills or barriers or axial potential wells which are preferably created within the ion guide 6 is preferably set such that ions preferably will not be able to substantially slip over a potential hill or barrier or be able to move or pass from one axial potential well to another. Ions are therefore preferably trapped within an axial potential well which is preferably translated along the length of the ion guide 6. The ions are preferably trapped and translated along the ion guide 6 preferably regardless of their mass, mass to charge ratio or ion mobility. The preferred ion guide 6 therefore preferably has the advantageous effect of preserving the order in which ions are received by the ion guide 6 from the upstream ion mobility spectrometer or separator 4 and also of preserving the composition of ions as they are received from the ion mobility spectrometer or separator 4. Ions received by the ion guide 6 from the ion mobility spectrometer or separator 4 are therefore preferably partitioned in the ion guide 6 and the partitioning of the ions maintains the separation of the ions according to their ion mobility. There is therefore preferably a direct correspondence between the ions trapped in the ion guide 6 and the ions emerging from the exit of the preferred ion mobility spectrometer or separator 4.

The ion guide 6 preferably also acts as an interface between the ion mobility spectrometer or separator 4 which may preferably be maintained at a relatively high pressure and other components of the mass spectrometer such as the downstream mass analyser 13 which are preferably maintained at substantially lower pressures. The ion guide 6 may therefore have the function of maintaining the fidelity of packets or groups of ions received from the ion mobility spectrometer or separator 4 and also of communicating these ions from a relatively high pressure region (e.g. the ion mobility spectrometer or separator 4) to a relatively low pressure region (e.g. a mass analyser 13).

According to an embodiment the ion guide 6 preferably transmits ions without substantially fragmenting them. However, according to alternative embodiments, ions may be accelerated out of the ion mobility spectrometer or separator 4 and into the ion guide 6 with sufficient kinetic energy such that the ions are caused to collide with gas molecules present in the ion guide 6 such that they are caused to fragment into daughter, fragment or product ions. Subsequent mass analysis of the daughter, fragment or product ions enables valuable mass spectral information about the parent or precursor ion(s) to be obtained.

The kinetic energy of ions entering the ion guide 6 can be controlled, for example, by setting or controlling the level of a potential difference or electric field experienced by the ions emerging from the ion mobility spectrometer or separator 4 immediately prior to entering the ion guide 6. The level of the potential difference or electric field may preferably be switched near instantaneously. According to an embodiment the level of the potential difference or electric field can be repeatedly and/or regularly switched between a first level wherein the potential difference or electric field is relatively high and a second level wherein the potential difference or electric field is relatively low. Accordingly, ions may be caused to be fragmented as they enter the ion guide 6 when the potential difference or electric field is at the first level and wherein the potential difference or electric field is relatively high. Conversely, ions will not be substantially fragmented when the potential difference or electric field is at the second level and wherein the potential difference or electric field is relatively low. Accordingly, the ion guide 6 may therefore effectively be switched regularly and repeatedly back and forth between a mode of operation wherein parent or precursor ions are transmitted by the ion guide 6 substantially without being fragmented and another mode of operation wherein parent or precursor ions are caused to fragment upon entering the ion guide 6.

The voltage or potential difference or electric field experienced by the ions prior to entering the ion guide 6 may also be varied (e.g. progressively increased) as ions progressively emerge from the exit of the ion mobility spectrometer or separator 4 and preferably before a further pulse of ions is admitted or otherwise injected into the ion mobility spectrometer or separator 4. The voltage or potential difference or electric field may be set such that the kinetic energy of one or more species of ion emerging from the ion mobility spectrometer or separator 4 is preferably optimised for fragmentation as the ions enter the ion guide 6. Alternatively, the voltage or potential difference or electric field may be progressively varied as ions exit the ion mobility spectrometer or separator 4 such that the collision energy is approximately or substantially optimised for all species of ions as the ions emerge from the exit of the ion mobility spectrometer or separator 4 and enter the ion guide 6.

According to a preferred embodiment transfer optics or an ion optical lens arrangement 8 may optionally be provided preferably in a further vacuum chamber downstream of the vacuum chamber housing the ion guide 6. The transfer optics or ion optical lens arrangement 8 may comprise an Einzel electrostatic lens. A differential pumping aperture 7 may be provided between the vacuum chamber housing the ion guide 6 and the vacuum chamber housing the transfer optics or ion optical lens arrangement 8. The transfer optics or ion optical lens arrangement 8 is preferably arranged to accelerate and guide ions through a further differential pumping aperture 9 and into a vacuum chamber housing the mass analyser 13. The vacuum chamber housing the transfer optics or ion optical lens arrangement 8 preferably acts as an intermediate region or interface between the ion guide 6 which may, for example, be maintained at a relatively intermediate pressure and the mass analyser 13 which is preferably maintained at a relatively low pressure.

According to a particularly preferred embodiment the mass analyser may comprise an orthogonal acceleration Time of Flight mass analyser 13 comprising a pusher and/or puller electrode 10 for injecting ions into an orthogonal drift or time of flight region. A reflection 11 may be provided for reflecting ions which have travelled through the orthogonal drift or time of flight region back towards an ion detector 12 which is preferably arranged in proximity to the pusher and/or puller electrode 10.

As is well known in the art, at least some of the ions in a packet of ions pulsed into an orthogonal acceleration Time of Flight mass analyser 13 are preferably caused to be orthogonally accelerated into the orthogonal drift or time of flight region. Ions become temporally separated as they pass through the orthogonal drift or time of flight region in a manner which is dependent upon their mass to charge ratio. Ions having a relatively low mass to charge ratio will travel faster in the drift or time of flight region than ions having a relatively high mass to charge ratio. Ions having a relatively low mass to charge ratio will therefore reach the ion detector 12 before ions having a relatively high mass to charge ratio. The time taken by an ion to drift through the drift or time of flight region and to reach the ion detector 12 is used to determine accurately the mass to charge ratio of the ion in question. The mass to charge ratios of the ions and the number of ions detected for each species of ion is preferably used to produce a mass spectrum.

In a conventional mass spectrometer it is known to store ions in an ion trap upstream of an orthogonal acceleration Time of Flight mass analyser. The ions are then non-mass selectively ejected from the ion trap so that all of the ions pass from the ion trap into the mass analyser. The ions in the packet of ions ejected from the ion trap will then become spatially dispersed by the time that the ions arrive at the orthogonal acceleration region of the mass analyser which is adjacent the pusher electrode. Accordingly, ions having a relatively low mass to charge ratio will reach the orthogonal acceleration region adjacent the pusher electrode before ions having a relatively high mass to charge ratio. The pusher electrode is energised so as to orthogonally accelerate some ions into the orthogonal acceleration region or drift region of the Time of Flight mass analyser at a predetermined time after the ions have first been released from the ion trap upstream of the mass analyser. Since the time of arrival of an ion at the orthogonal acceleration region adjacent the pusher electrode of the mass analyser is dependent upon the mass to charge ratio of the ion, then appropriate setting of the time delay between ions being released from the ion trap and ions being orthogonally accelerated ensures that ions having a certain mass to charge ratio will be injected by the pusher electrode into the orthogonal acceleration Time of Flight mass analyser with a relatively high sampling duty cycle. However, other ions will either have passed beyond the orthogonal acceleration region adjacent the pusher electrode at the time when the pusher electrode is energised or they will not yet have reached the orthogonal acceleration region adjacent the pusher electrode at the time when the pusher electrode is energised. Accordingly, these ions will not be orthogonally accelerated into the orthogonal acceleration drift region and hence these ions will be lost to the system.

Figure 8:
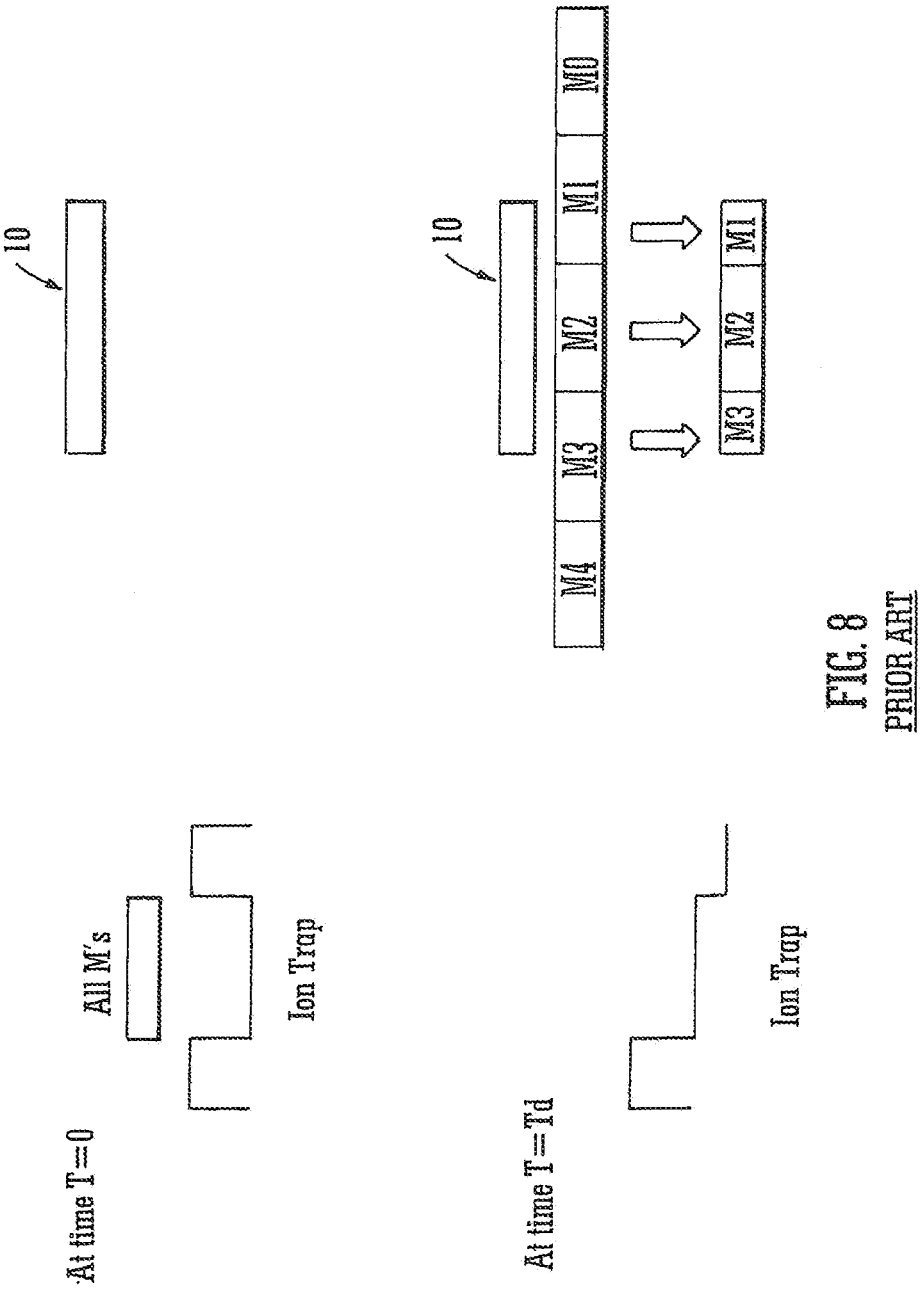
FIG. 8 illustrates a conventional arrangement wherein ions having a relatively wide range of mass to charge ratios are non-mass selectively released from an ion trap upstream of an orthogonal acceleration Time of Flight mass analyser and will have a spatial spread which exceeds the width of the orthogonal acceleration region of a Time of Flight mass analyser by the time that the ions reach the orthogonal acceleration region.

FIG. 8 illustrates in more detail how conventionally the timing of the energisation of the pusher electrode 10 has the effect of only orthogonally accelerating some ions having a specific mass to charge ratio when a group of ions is non-mass selectively pulsed out of an ion trap and into an orthogonal acceleration Time of Flight mass analyser. At an initial time T=0 ions having a wide range of mass to charge ratios are non-mass selectively released from the ion trap upstream of the orthogonal acceleration Time of Flight mass analyser. After a period of time Td, ions having a mass to charge ratio M2 will have reached the orthogonal acceleration region adjacent the pusher electrode 10. If the pusher electrode 10 is then energised at this instant, then all of the ions having a mass to charge ratio M2 will be injected or will be otherwise orthogonally accelerated into the orthogonal drift or time of flight region of the Time of Flight mass analyser. This will result in a sampling duty cycle of substantially 100% for ions having a mass to charge ratio M2. However, ions having a substantially greater mass to charge ratio M4 (M4>M2) will not yet have reached the orthogonal acceleration region adjacent the pusher electrode 10 when the pusher electrode 10 is energised. Accordingly, ions having a mass to charge ratio M4 will not be injected or otherwise be orthogonally accelerated into the orthogonal acceleration region of the Time of Flight mass analyser. Similarly, ions having a substantially lower mass to charge ratio M0 (M0<M2) will have already passed the orthogonal acceleration region adjacent the pusher electrode 10 when the pusher electrode 10 is energised. Accordingly, ions having a mass to charge ratio M0 will also not be injected or otherwise be orthogonally accelerated into the orthogonal acceleration region of the Time of Flight mass analyser. The sampling duty cycle for ions having a mass to charge ratio of M0 and M4 will therefore be 0%.

Ions having intermediate mass to charge ratios M3 and M1 (M2<M3<M4 and M0<M1<M2) will only be partially injected or otherwise orthogonally accelerated into the orthogonal drift region of the Time of Flight mass analyser. The duty cycle for ions having a mass to charge ratio of M1 and M3 will therefore be somewhere between 0% and 100%.

By adjusting the time delay Td between the time when the pusher electrode 10 is energised relative to the time when ions are released from the ion trap into the mass analyser, it is possible to optimise the transmission and orthogonal acceleration of certain ions having certain mass to charge ratios.

Figure 9:
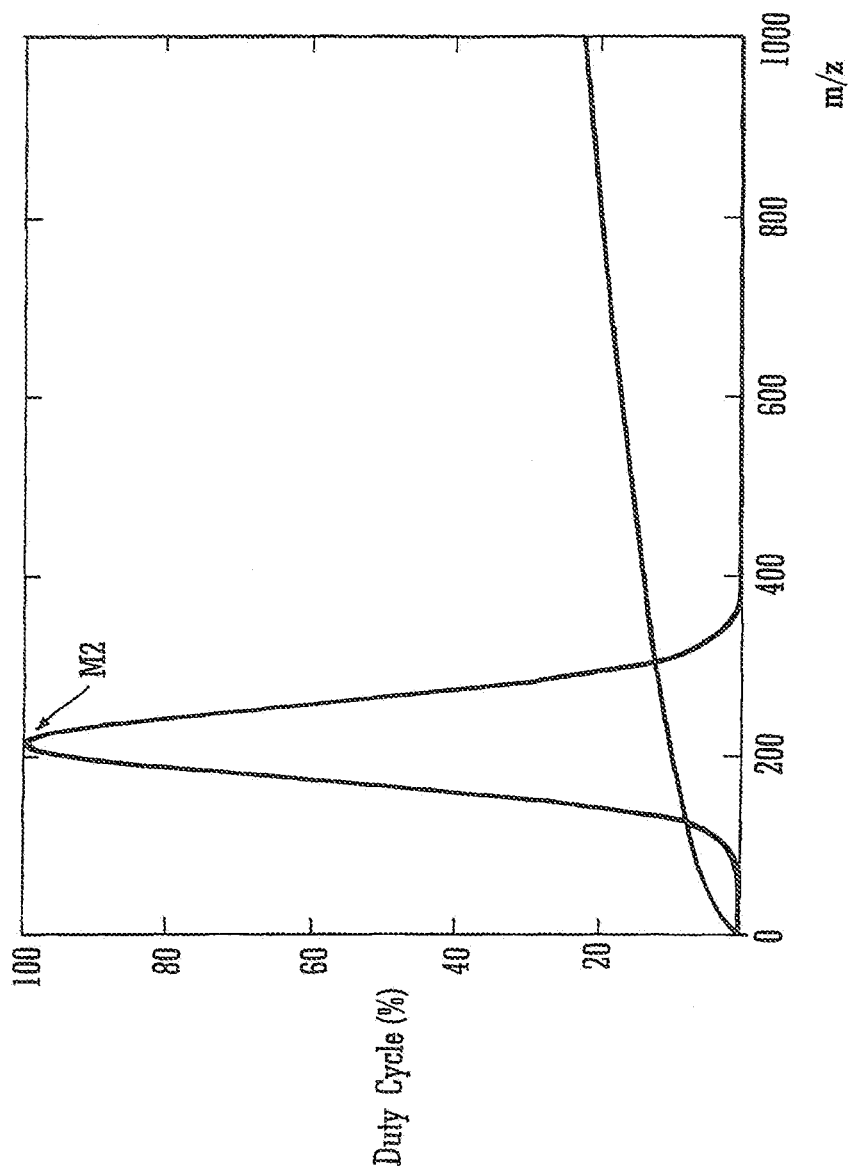
FIG. 9 illustrates the relatively low sampling duty cycle obtained when ions are continuously passed into a Time of Flight mass analyser and ions are periodically sampled and also how pulsing ions into a Time of Flight mass analyser and setting an appropriate delay time of the orthogonal acceleration pulse enables the sampling duty cycle to be increased only for some ions.

The lower curve in FIG. 9 shows the sampling duty cycle for a conventional mass spectrometer when a continuous beam of ions is transmitted into an orthogonal acceleration Time of Flight mass analyser. The pusher electrode of the mass analyser is repeatedly pulsed to sample the ion beam and the sampling duty cycle is relatively low (0-20%) across the whole of the mass to charge ratio range of interest. FIG. 9 also shows how the sampling duty cycle for ions having a certain mass to charge ratio of M2 can be increased to substantially 100% by pulsing ions into the mass analyser and then setting the time delay between the pulsing of ions into the mass analyser and energising the pusher electrode. However, although the sampling duty cycle for ions having a mass to charge ratio of M2 is increased, this approach suffers from the problem that the sampling duty cycle for other ions having other mass to charge ratios rapidly tails off to 0%.

The preferred embodiment enables the sampling duty cycle across substantially the whole mass to charge ratio range of interest to be increased rather than just enhancing the sampling duty cycle for a narrow range of ions having a narrow range of mass to charge ratios.

Figure 10:
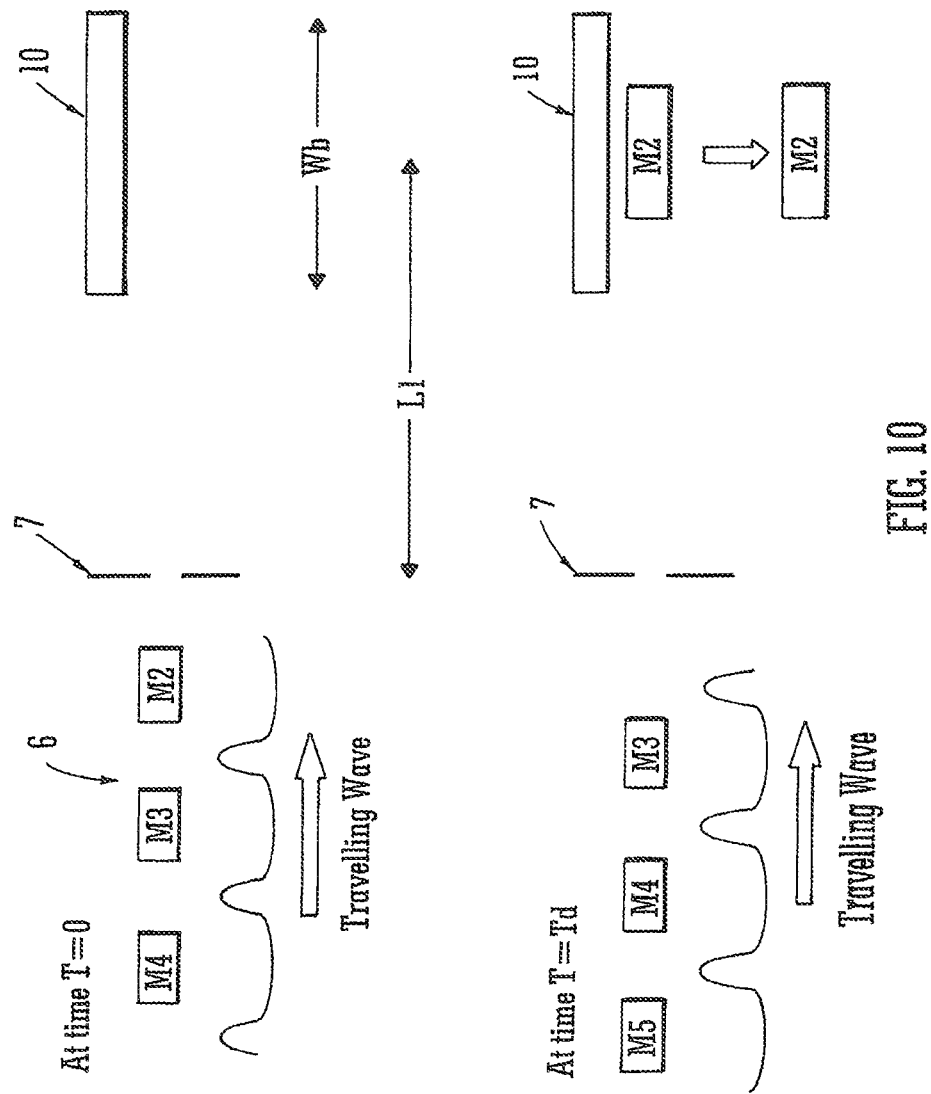
FIG. 10 shows how ions which are released from an axial potential well at the exit of an ion guide according to the preferred embodiment of the present invention do not become significantly spatially separated by the time that the ions reach the orthogonal acceleration region of an orthogonal acceleration Time of Flight mass analyser since the ions in each packet of ions released from the ion guide will have substantially similar mass to charge ratios.

The manner of operation of the preferred embodiment of the present invention will now be described in more detail with reference to FIG. 10. FIG. 10 illustrates an ion guide 6 located downstream of an ion mobility spectrometer or separator and upstream of an orthogonal acceleration Time of Flight mass analyser. One or more transient DC voltages or one or more transient DC voltage waveforms are preferably applied to the electrodes of the ion guide 6 so that one or more axial potential wells are created in the ion guide 6. The one or more axial potential wells are then preferably moved or are otherwise translated from the entrance region of the ion guide 6 to the exit region of the ion guide 6. Packets of ions are then sequentially elected from the exit region of the ion guide 6.

According to the preferred embodiment the timing of the energisation of the pusher electrode 10 of the Time of Flight mass analyser arranged downstream of the ion guide 6 is preferably set such that all the ions released from an axial potential well which has reached the end of the ion guide 6 are then preferably subsequently orthogonally accelerated into an orthogonal acceleration or drift region of the mass analyser.

FIG. 10 shows schematically packets or groups of ions being translated along the length of the ion guide 6. An exit aperture or region 7 is shown at the exit of the ion guide 6 and which is upstream of an orthogonal acceleration Time of Flight mass analyser comprising a pusher electrode 10. The centre of the pusher electrode 10 is preferably arranged at an axial distance L1 from the exit aperture or region 7 of the ion guide 6. The pusher electrode 10 preferably has a width Wb.

At a time T=0 a first packet of ions comprising ions contained within an first axial potential well which has preferably reached the exit region of the ion guide 6 is released from the on guide 6. The ions released from the first axial potential well preferably all have a mass to charge ratio of substantially M2 and preferably pass towards the pusher electrode 10. After a period of time Td the ions having a mass to charge ratio M2 will preferably have reached the orthogonal acceleration region adjacent the centre of the pusher electrode 10. The pusher electrode 10 is then preferably energised so that all the ions having a mass to charge ratio M2 are then preferably injected or are otherwise orthogonally accelerated into the orthogonal drift region of the Time of Flight mass analyser 13. The distance L1 between the exit of the ion guide 6 and the centre of the pusher electrode 10 is preferably arranged so as to be relatively short. The pusher electrode 10 is also preferably arranged so as to have a suitably wide width Wb such that the spatial spread of ions having a mass to charge ratio M2 when they arrive at the orthogonal acceleration region is preferably smaller than the width Wb of the pusher electrode 10. Accordingly, the sampling duty cycle for the ions having a mass to charge ratio M2 is preferably substantially 100%.

At a later time a second packet of ions is then preferably released from a second axial potential well which has preferably now reached the exit region of the ion guide 6. The ions released from the second axial potential well preferably have a mass to charge ratio of substantially M3 which is preferably at least slightly greater than M2. This is because the ions contained in each axial potential well reflect the order in which ions are received from the ion mobility spectrometer or separator 4 and the mass to charge ratio of ions emerging from the ion mobility spectrometer or separator 4 preferably increases with time. The ions having a mass to charge ratio M3 are then preferably ejected from the ion guide 6 and preferably move towards the pusher electrode 10. The pusher electrode 10 is then preferably energised after a time delay which is preferably slightly greater than Td. This reflects the fact that the ions have a slightly greater mass to charge ratio M3 than the ions in the first packet having a mass to charge ratio M2 and will therefore take slightly longer to reach the orthogonal acceleration region adjacent pusher electrode 10.

The process is then preferably repeated in a similar manner for a third packet of ions comprising ions having a mass to charge ratio of substantially M5 (wherein M5>M4>M3) which are preferably released from a third axial potential well when that axial potential well preferably reaches the exit region of the ion guide 6.

Embodiments are contemplated wherein, for example, 200 or more separate packets of ions may be successively released from separate axial potential wells which successively reach the end of the ion guide 6 during the course of a single cycle of pulsing ions into the ion mobility spectrometer or separator 4. For sake of illustration only, the ion mobility spectrometer or separator 4 may have a cycle time of 10 ms i.e. ions are pulsed into the ion mobility spectrometer or separator 4 and may take up to 10 ms to emerge from the ion mobility spectrometer or separator 4. The ions emerging from the ion mobility spectrometer or separator 4 over the period of 10 ms may be arranged to be collected or trapped in one of 200 successive axial potential wells which are preferably created in the ion guide 6. Each axial potential well is then preferably subsequently translated along the length of the ion guide 6 from the entrance region of the ion guide 6 to the exit region of the ion guide 6. Each axial potential well formed in the ion guide 6 may therefore take approximately 50 µs to move or otherwise be translated from the entrance region of the ion guide 6 to the exit region of the ion guide 6.

For each packet of ions released from an axial potential well which has been translated from the entrance region to the exit region of the ion guide 6, a corresponding optimum delay time between the release of the ions from the ion guide 6 and the energisation of the pusher electrode 10 is preferably determined and set. The delay time between the release of a packet of ions from the exit of the ion guide 6 and the application of an orthogonal acceleration pusher voltage to the pusher electrode 10 is preferably progressively increased to reflect the fact that the ions trapped in the initial axial potential wells created in the ion guide 6 will have relatively low mass to charge ratios whereas ions subsequently received from the ion mobility spectrometer or separator 4 at a later time and which are trapped in subsequently created axial potential wells will have relatively high mass to charge ratios.

Figure 11:
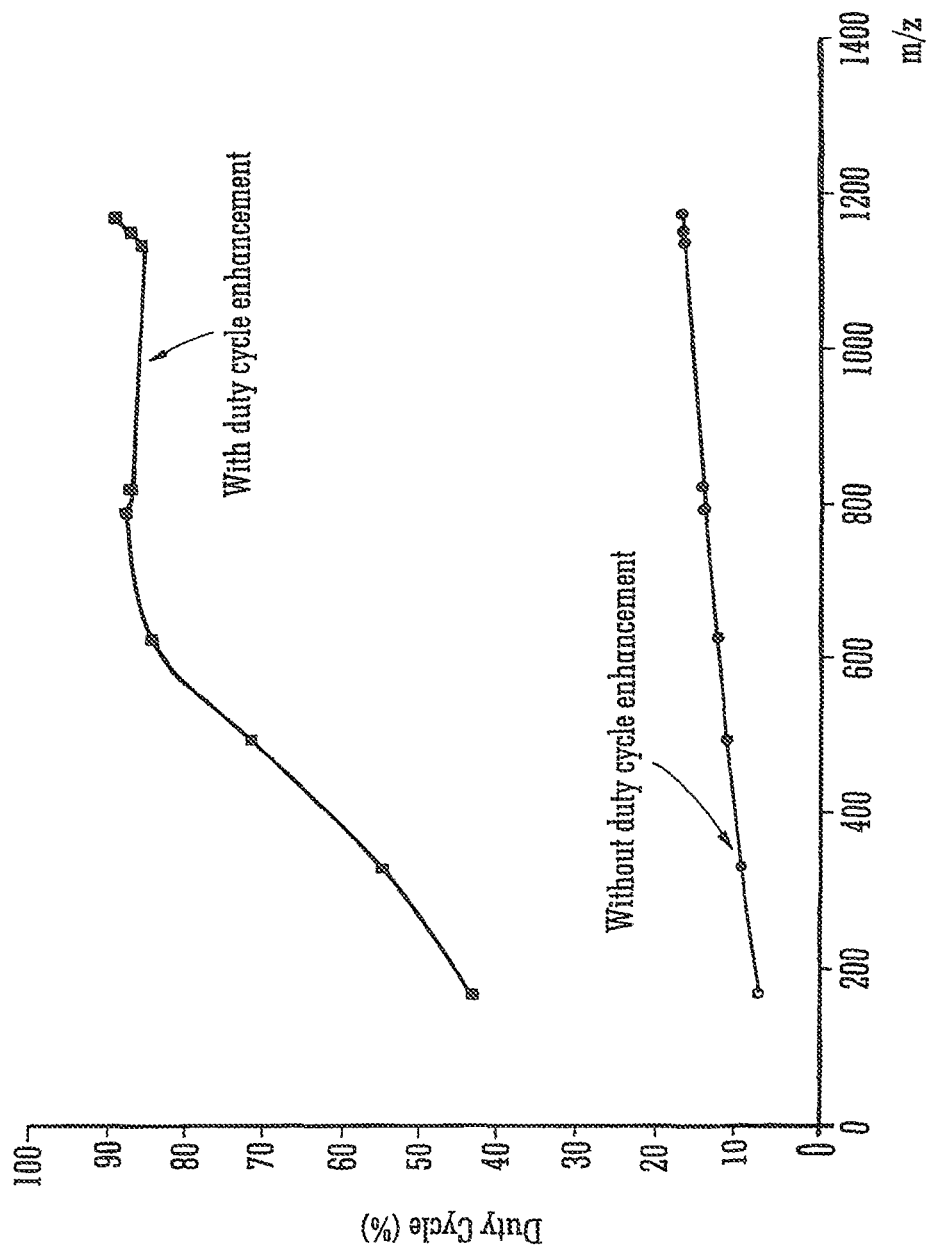
FIG. 11 shows some experimental results and demonstrates how the sampling duty cycle can be significantly improved to >80% for ions having a wide range of mass to charge ratios according to an embodiment of the present invention whereas the typical average conventional sampling duty cycle is only approximately 15%.

FIG. 11 shows some experimental results which illustrate the significant enhancement in sampling duty cycle which is obtainable according to the preferred embodiment. It is to be noted that advantageously an enhancement in sampling duty cycle is obtained over the whole of the mass to charge ratio range of interest rather than just over a relatively narrow mass to charge ratio range. The sampling duty cycle as shown in FIG. 11 relates to all doubly charged analyte ions which were observed. FIG. 11 also shows for comparison purposes the sampling duty cycle measured when the same sample was analysed by passing a continuous ion beam into the mass analyser and repeatedly pulsing the pusher electrode.

Figure 12:
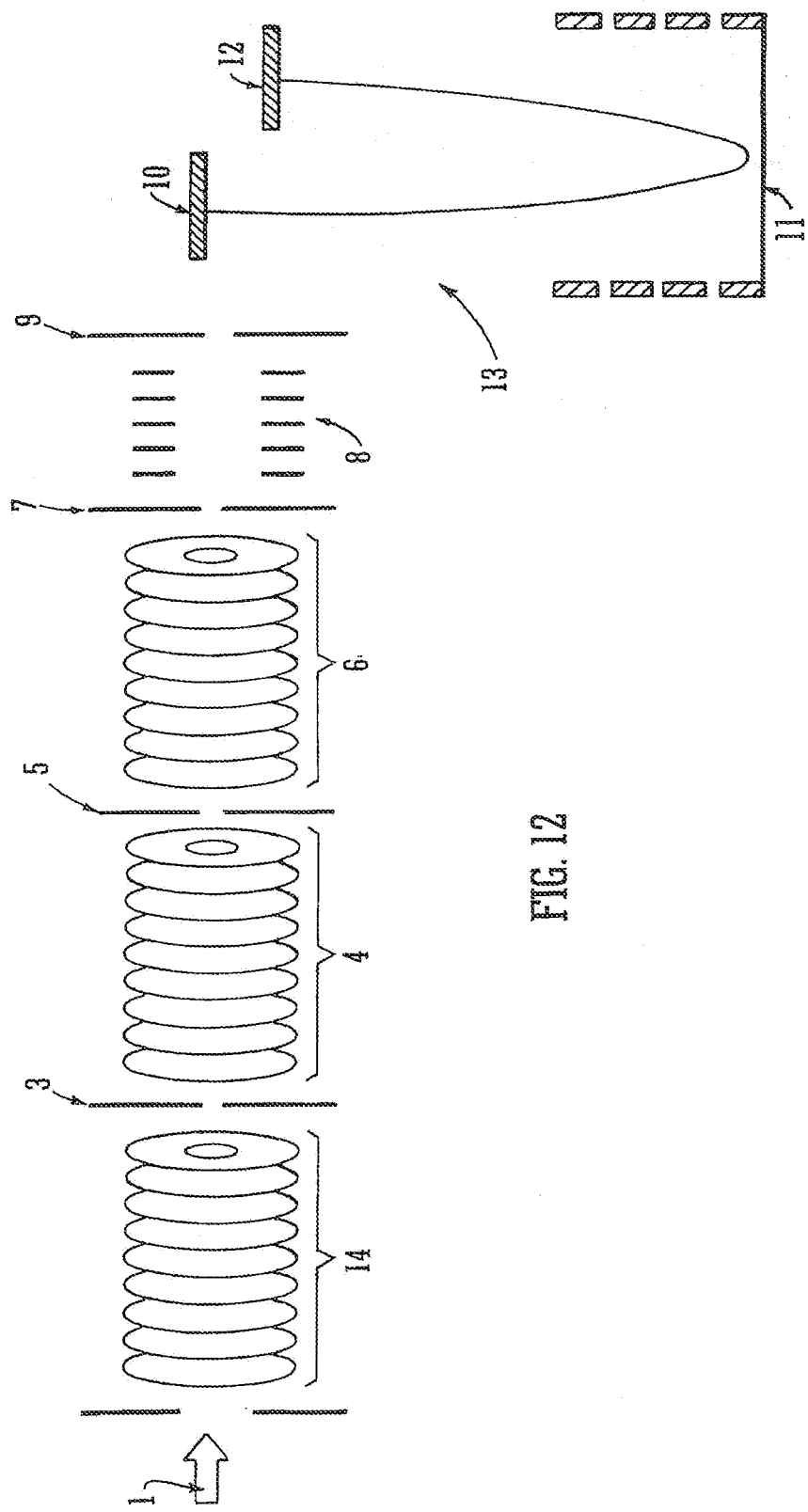
FIG. 12 shows a second preferred embodiment of the present invention wherein a second ion guide is provided upstream of the ion mobility spectrometer or separator and wherein a plurality of axial potential wells are preferably created within and translated along the length of the second ion guide.

FIG. 12 shows a second embodiment of the present invention. The second embodiment differs from the first embodiment as described above with reference to FIG. 6 in that the optional ion trap 2 provided upstream of the ion mobility spectrometer or separator 4 in the first embodiment is preferably replaced with a second ion guide 14. The second embodiment is otherwise preferably substantially similar to the first embodiment. The ion mobility spectrometer or separator 4 and the ion guide 6 provided downstream of the ion mobility spectrometer or separator 4 preferably take one of the forms as described above in relation to the first embodiment of the present invention as described with reference to FIG. 6. The various different ion sources described above in relation to the first embodiment may also be used in relation to the second embodiment. The second ion guide 14 may take the same form as the ion guide 6 arranged downstream of the ion mobility spectrometer or separator 4 and as described in reference to the first embodiment.

The second ion guide 14 is preferably provided upstream of the ion mobility spectrometer or separator 4 and preferably comprises a plurality of electrodes having apertures through which ions are preferably transmitted in use. The apertures of the electrodes forming the second ion guide 14 are preferably substantially all the same size. In other embodiments at least 60%, 65%, 70%, 75%, 80%, 85%, 90% or 95% of the electrodes of the second ion guide 14 have apertures which are substantially the same size. Adjacent electrodes of the second ion guide 14 are preferably connected to the opposite phases of a two-phase AC or RF supply.

According to the second embodiment one or more transient DC voltages or potentials or one or more transient DC voltage or potential waveforms are preferably applied to the electrodes of the second ion guide 14 in order to form one or more potential hills or barriers. The one or more transient DC voltages or potentials or one or more transient DC voltage or potential waveforms are preferably progressively applied to a succession of electrodes of the second ion guide 14 such that one or more potential hills or barriers move along the axis of the second ion guide 14 towards an exit region of the second ion guide 14.

The second ion guide 14 is preferably provided in a vacuum chamber or is otherwise preferably maintained, in use, at a pressure within the range 0.001-0.01 mbar. According to less preferred embodiments, the second ion guide 14 may be maintained at a pressure greater than 0.01 mbar up to a pressure at or near 1 mbar. According to less preferred embodiments the second ion guide 14 may alternatively be maintained at a pressure below 0.001 mbar.

The gas pressure at which the second ion guide 14 is preferably maintained and is preferably sufficient to impose collisional damping of ion motion but is preferably not sufficient so as to impose excessive viscous drag upon the movement of ions. The amplitude and average velocity of the one or more potential hills or barriers created within the second ion guide 14 is preferably set such that ions preferably will not substantially slip or otherwise move over a potential hill or barrier. Ions are therefore preferably trapped in one or more axial potential wells which are preferably translated along the length of the second ion guide 14. Ions are preferably trapped and transported regardless of their mass, mass to charge ratio or ion mobility.

The pressure in the second ion guide 14 may be the same as the pressure in the ion guide 6 arranged downstream of the ion mobility spectrometer or separator 4. In a preferred embodiment the second ion guide 14 provided upstream of the ion mobility spectrometer or separator 4 and the ion guide 6 provided downstream of the ion mobility spectrometer or separator 4 may be provided in the same vacuum chamber. The intermediate ion mobility spectrometer or separator 4 may be contained within a separate housing positioned within the vacuum chamber containing the ion guide 6 provided downstream of the ion mobility spectrometer or separator 4 and the second ion guide 14 provided upstream of the ion mobility spectrometer or separator 4. A collision gas, preferably nitrogen or argon, may be supplied to the housing containing the ion mobility spectrometer or separator 4 in order to maintain the ion mobility spectrometer or separator 4 at a relatively high pressure. The housing containing the ion mobility spectrometer or separator 4 may be maintained, for example, at a pressure between 0.1 and 10 mbar. The collision gas present in the housing containing the ion mobility spectrometer or separator 4 may be allowed to leak into the vacuum chamber containing the second ion guide 14 and the ion guide 6 arranged downstream of the ion mobility spectrometer or separator 4 through an entrance and exit aperture in the housing as shown schematically in FIG. 7A. The vacuum chamber containing the housing is preferably pumped such as to maintain the pressure in the vacuum chamber within the range 0.001 and 0.01 mbar.

Ions may be transported in and along the second ion guide 14 and may preferably be released as packets of ions into or towards the ion mobility spectrometer or separator 4 which is preferably arranged downstream of the second ion guide 14. The cycle time of the second ion guide 14 (i.e. the time taken for an axial potential well to be translated along the length of the second ion guide 14) may preferably be equal to or substantially similar to the cycle time of the ion mobility spectrometer or separator 4. Alternatively, ions may be accumulated and held in an ion trapping region provided preferably near the exit of the second ion guide 14. The ions may then be released from the second ion guide 14 into or towards the ion mobility spectrometer or separator 4 at the start of each cycle of the ion mobility spectrometer or separator 4. In this mode of operation the cycle time of translating axial potential wells along the length of the second ion guide 14 the second ion guide 14 does not need to be match the cycle time of the ion mobility spectrometer or separator 4.

In one mode of operation ions may be arranged such that they are sufficiently energetic when they enter the second ion guide 14 that they collide with gas molecules present in the second ion guide 14 and are caused to fragment into daughter, fragment or product ions. The daughter, fragment or product ions may then be passed or onwardly transmitted to the ion mobility spectrometer or separator 4. The daughter, fragment or product ions may then be subsequently separated according to their ion mobility in the ion mobility separator or spectrometer 4. The daughter, fragment or product ions may then preferably be ejected from or otherwise emerge from the ion mobility spectrometer or separator 4 and are preferably received and trapped in a plurality of axial potential wells generated in the ion guide 6 which is preferably located downstream of the ion mobility spectrometer or separator 4. Packets of ions are then preferably ejected from the ion guide 6 and are preferably subsequently mass analysed by the orthogonal acceleration Time of Flight mass spectrometer 13.

The energy of ions entering the second ion guide 14 may be controlled, for example, by setting the level of a voltage or potential difference or electric field experienced by the ions prior to entering the second ion guide 14. Since the voltage or potential difference or electric field can be switched near instantaneously, the second ion guide 14 can be regularly and repeatedly switched between a relatively high fragmentation mode of operation and a relatively low fragmentation mode of operation.

The voltage or potential difference or electric field experienced by the ions prior to entering the second ion guide 14 may also be switched alternately between a relatively low level and a relatively high level upon successive cycles of pulsing ions into the ion mobility spectrometer or separator 4.

In yet another mode of operation daughter, fragment or product ions emerging from the ion mobility spectrometer or separator 4 may be arranged such that they are sufficiently energetic that when they enter the ion guide 6 arranged downstream of the ion mobility spectrometer or separator 4 they themselves are then caused to collide with gas molecules present in the ion guide 6 and are caused to further fragment into grand-daughter or second generation fragment ions. Subsequent mass analysis of the grand-daughter or second generation fragment ions yields valuable information about the related parent and/or daughter ion(s).

The energy of ions entering the ion guide 6 downstream of the ion mobility spectrometer or separator 4 can be controlled, for example, by setting the level of a voltage or potential difference or electric field experienced by the ions prior to entering the ion guide 6. Since the voltage or potential difference or electric field can be switched near instantaneously, the ion guide 6 can be repeatedly and regularly switched between a first mode wherein parent or daughter ions are fragmented and a second mode wherein parent or daughter ions are not substantially fragmented.

The voltage or potential difference or electric field experienced by the ions prior to entering the ion guide 6 arranged downstream of the ion mobility spectrometer or separator 4 may also be varied as ions progressively emerge from the ion mobility spectrometer or separator 4. The voltage or potential difference or the electric field may be set such that the collision energy is optimised for one or more species of parent or daughter ions as ions emerge from the ion mobility spectrometer or separator 4. Alternatively, the voltage or potential difference or the electric field may be progressively varied (e.g. increased) as ions emerge from the ion mobility spectrometer or separator 4 such that the collision energy is approximately optimised for all species of parent or daughter ions as ions emerge from the ion mobility spectrometer or separator 4.

The voltage or potential difference or electric field experienced by the parent or daughter ions prior to entering the ion guide 6 arranged downstream of the ion mobility spectrometer or separator 4 may also be switched alternately between a relatively low level and a relatively high level upon successive cycles of ions being pulsed into the ion mobility spectrometer or separator 4.

Some experimental results are shown in FIGS. 13A and 13B. FIG. 13A shows a mass spectrum of a peptide mixture which has been mass analysed in a conventional manner. The sampling duty cycle was not enhanced and the mass spectral data was not post-processed in order to produce a mass spectrum relating just to ions having a particular charge state. FIG. 13B shows a comparable mass spectrum wherein the sampling duty cycle was enhanced according to the preferred embodiment. As can be seen from comparing FIGS. 13A and 13B, the preferred approach to enhancing the sampling duty cycle according to the preferred embodiment resulted in the sensitivity being increased by a factor of approximately ×6 across the whole mass to charge ratio range of interest. As can be seen from FIG. 13B, the preferred embodiment enables a significant improvement in the art to be achieved.

Figures 14A, 14B, 14C:
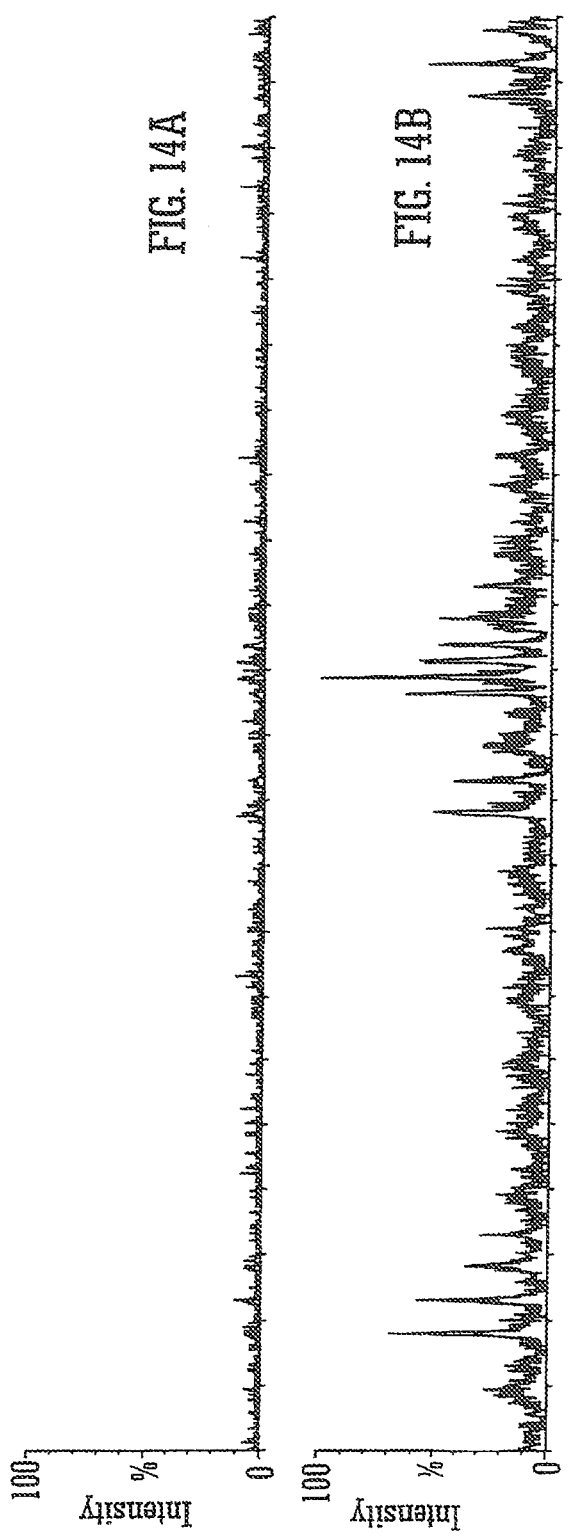
FIG. 14A shows in greater detail a portion of the mass spectrum obtained conventionally and which is shown in FIG. 13A.
FIG. 14B shows in greater detail a corresponding portion of the mass spectrum obtained by enhancing the sampling duty cycle in a manner according to an embodiment of the present invention and FIG. 14C shows a corresponding portion of a mass spectrum obtained according to a particularly preferred embodiment of the present invention wherein the sampling duty cycle was enhanced in a manner according to an embodiment of the present invention and wherein the mass spectral data was also post-processed so that only ions having a particular charge state were displayed in the final mass spectrum.

FIGS. 14A-C show a small portion of the mass spectrum shown in FIGS. 13A and 13B in greater detail across the mass to charge ratio range 658-680. FIG. 14A shows a portion of the mass spectrum obtained in a conventional manner. FIG. 14B shows a corresponding mass spectrum obtained by enhancing the sampling duty cycle according to the preferred embodiment. FIG. 14C shows an additional increase or improvement in the signal to noise ratio obtained by further post-processing the mass spectral data which was acquired in order to remove mass spectral data relating to singly charged background ions. This was achieved by exploiting the relationship between the mass to charge ratio of ions and their drift time through the ion mobility spectrometer or separator which depends upon the charge state of the ions.

Figures 15A, 15B, 15C:
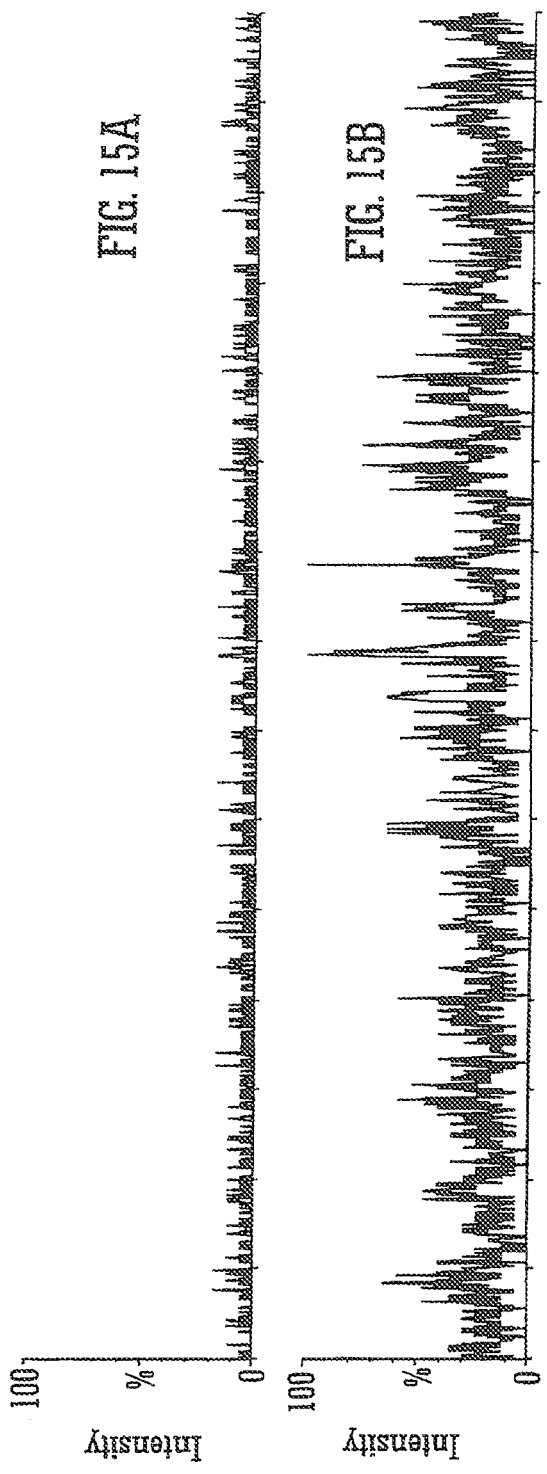
FIG. 15A shows in greater detail a different portion of the mass spectrum obtained conventionally and which is shown in FIG. 13A.
FIG. 15B shows in greater detail a corresponding portion of the mass spectrum obtained by enhancing the sampling duty cycle in a manner according to an embodiment of the present invention and FIG. 15C shows a corresponding portion of a mass spectrum obtained according to a particularly preferred embodiment of the present invention wherein the sampling duty cycle was enhanced in a manner according to an embodiment of the present invention and wherein the mass spectral data was also post-processed so that only ions having a particularly charge state were displayed in the final mass spectrum.

FIGS. 15A-C show another small portion of the mass spectrum shown in FIGS. 13A and 13B in greater detail across the mass to charge ratio range 780-795. FIG. 15A shows a portion of the mass spectrum obtained in a conventional manner. FIG. 15B shows a corresponding mass spectrum obtained by enhancing the sampling duty cycle according to the preferred embodiment. FIG. 15C shows an additional increase or improvement in the signal to noise ratio obtained by further post-processing the mass spectral data to remove mass spectral data relating to singly charged background ions. This was achieved by exploiting the relationship between the mass to charge ratio of ions and their drift times through an ion mobility spectrometer or separator which depends upon the charge state of the ions.

According to a particularly preferred embodiment an Atmospheric Pressure Ionisation ion source may be provided. A relatively high pressure (e.g. $>10^{-3}$ mbar) ion guide may be arranged to receive ions from the ion source. The ion guide preferably comprises a plurality of electrodes having apertures through which ions are transmitted in use. One or more transient DC voltages or potentials or one or more transient DC voltage or potential waveforms are preferably applied to the electrodes of the ion guide. A relatively low pressure (e.g. $<10^{-3}$ mbar) quadrupole rod set mass filter is preferably arranged downstream of the ion guide.

A further ion guide is preferably arranged downstream of the mass filter and preferably comprises a plurality of electrodes having apertures through which ions are transmitted in use. One or more transient DC voltages or potentials or one or more transient DC voltage or potential waveforms are preferably applied to the electrodes of the further ion guide. The further ion guide is preferably maintained at a relatively high pressure (e.g. $>10^{-3}$ mbar) and ions may be fragmented and/or trapped within the further ion guide.

An ion mobility spectrometer or separator is preferably arranged downstream of the further ion guide and ions are preferably pulsed out of the further ion guide into the ion mobility spectrometer or separator. The ion mobility spectrometer or separator preferably comprises a plurality of electrodes having apertures through which ions are transmitted in use. One or more transient DC voltages or potentials having a relatively low amplitude or one or more transient DC voltage or potential waveforms having a relatively low amplitude are preferably applied to the electrodes of the ion mobility spectrometer or separator in order to separate ions according to their ion mobility. The ion mobility spectrometer or separator is preferably maintained at a pressure $>10^{-2}$ mbar.

A yet further ion guide is preferably arranged downstream of the ion mobility spectrometer or separator in order to receive ions emerging from the ion mobility spectrometer or separator. The yet further ion guide preferably comprises a plurality of electrodes having apertures through which ions are transmitted in use. One or more transient DC voltages or potentials or one or more transient DC voltage or potential waveforms are preferably applied to the electrodes of the yet further ion guide. The yet further ion guide preferably maintains the fidelity and/or composition of the packets of ions which preferably emerge from the ion mobility spectrometer or separator.

A transfer optic is preferably arranged downstream of the yet further ion guide and preferably comprises an Einzel or other electrostatic lens arrangement. The transfer optic is preferably maintained at a relatively low or intermediate pressure (i.e. $<10^{-3}$ mbar) and preferably acts as a differential pressure pumping stage. An orthogonal acceleration Time of Flight mass analyser is preferably arranged downstream of the transfer optic and/or the yet further ion guide.

Although according to the preferred embodiment the AC or RF voltage applied to the electrodes of the ion mobility spectrometer or separator 4, the ion guide 6 downstream of the ion mobility spectrometer or separator and optionally the second ion guide 14 preferably has a sinusoidal waveform, other less preferred embodiments are contemplated wherein the AC or RF voltage supplied or applied to electrode(s) of the ion mobility spectrometer or separator 4 and/or the ion guide 6 downstream of the ion mobility spectrometer or separator 4 and/or the second ion guide 14 may be non-sinusoidal. For example, the AC or RF voltage may take the form of a square wave.

Although the present invention has been described with reference to preferred embodiments, it will be understood by those skilled in the art that various changes in form and detail may be made without departing from the scope of the invention as set forth in the accompanying claims.

The invention claimed is:

1. A mass spectrometer comprising:
    an ion mobility separator;
    an ion guide comprising a stack of electrodes arranged downstream of said ion mobility separator;
    a voltage source for applying one or more voltages to the stack of electrodes for generating an axial potential well and translating the axial potential well along the ion guide;
    a mass filter or a further ion guide;
    a fragmentation or collision cell for fragmenting ions; and
    a TOF mass analyser orthogonally disposed downstream of the ion guide.

2. A mass spectrometer as claimed in claim 1, wherein said mass filter comprises a quadrupole mass filter.

3. A mass spectrometer as claimed in claim 1, wherein said mass filter is arranged so that a mass filtering characteristic of said mass filter is progressively varied, increased or stepped.

4. A mass spectrometer as claimed in claim 3, wherein said mass filter is arranged so that ions having a first charge state are onwardly transmitted whereas ions having a second different charge state are substantially attenuated by said mass filter.

5. A mass spectrometer as claimed in claim 4, wherein said mass filter is arranged so that multiply charged ions are preferentially selected and are onwardly transmitted by said mass filter.

6. A mass spectrometer as claimed in claim 5, wherein said mass filter is arranged so that singly charged ions are reduced or substantially attenuated by said mass filter.

7. A mass spectrometer as claimed in claim 1, wherein said mass filter is operated as a high pass mass to charge ratio filter or a band pass mass to charge ratio filter.

8. A mass spectrometer as claimed in claim 1, wherein said fragmentation or collision cell comprises a Collision Induced Dissociation ("CID") for fragmenting ions upon colliding with or impacting gas or other molecules.

9. A mass spectrometer as claimed in claim 1, wherein said fragmentation or collision cell is selected from the group consisting of: (i) a Surface Induced Dissociation ("SID") fragmentation device; (ii) an Electron Transfer Dissociation fragmentation device; (iii) an Electron Capture Dissociation fragmentation device; (iv) an Electron Collision or Impact Dissociation fragmentation device; (v) a Photo Induced Dissociation ("PID") fragmentation device; (vi) a Laser Induced Dissociation fragmentation device; (vii) an infrared radiation induced dissociation device; (viii) an ultraviolet radiation induced dissociation device; (ix) an ion-molecule reaction fragmentation device; (x) a thermal or temperature source fragmentation device; (xi) an electric field induced fragmentation device; and (xii) a magnetic field induced fragmentation device.

10. A method of mass spectrometry employing mass spectrometry including an ion mobility separator, an ion guide including a stack of electrodes arranged downstream of said ion mobility separator, a voltage source for applying one or more voltages to the stack of electrodes for generating an axial potential well and translating the axial potential well along the ion guide, a mass filter or a further ion guide, a fragmentation or collision cell for fragmenting ions, and a TOF mass analyser orthogonally disposed downstream of the ion guide comprising:
    applying one or more voltages to the stack of electrodes to generate an axial potential well, and translate the axial potential well along the ion guide.

11. The method as claimed in claim 10, further comprising:
    progressively varying, increasing or stepping the filtering characteristic of the mass filter.

12. The method as claimed in claim 11 further comprising:
    onwardly transmitting ions having a first charge state through the mass filter; and
    substantially attenuating ions having a second charge state with the mass filter.

13. The method as claimed in claim 12 further comprising:
    preferably selecting and onwardly transmitting ions that are multiply charged through the mass filter.

14. The method according to claim 13 further comprising:
    reducing or substantially attenuating singly charged ions with said mass filter.

15. The method according to claim 10 further comprising:
    operating the mass filter as a high pass mass to charge ratio or as a band pass mass to charge ratio filter.

16. The method according to claim 10 further comprising:
    fragmenting ions with a fragmentation or collision cell by having the ions impact with gas or other molecules in the fragmentation or collision cell.

* * * * *

UNITED STATES PATENT AND TRADEMARK OFFICE
CERTIFICATE OF CORRECTION

| | | |
|---|---|---|
| PATENT NO. | : 8,569,687 B2 | Page 1 of 1 |
| APPLICATION NO. | : 13/663191 | |
| DATED | : October 29, 2013 | |
| INVENTOR(S) | : Bateman et al. | |

It is certified that error appears in the above-identified patent and that said Letters Patent is hereby corrected as shown below:

Title Page, item (72), line 4, the last name "Woldgoose" should be changed to --Wildgoose--.

Signed and Sealed this
Eleventh Day of February, 2014

Michelle K. Lee
*Deputy Director of the United States Patent and Trademark Office*